(12) United States Patent
Torrance et al.

(10) Patent No.: US 11,000,359 B2
(45) Date of Patent: May 11, 2021

(54) SYSTEMS, DEVICES, AND METHODS FOR COUPLING A PROSTHETIC IMPLANT TO A FENESTRATED BODY

(71) Applicant: Aortica Corporation, Bellevue, WA (US)

(72) Inventors: Casey Torrance, Snohomish, WA (US); Shannon Eubanks, Woodinville, WA (US); Edward Wulfman, Woodinville, WA (US); Thomas Douthitt, Kirkland, WA (US)

(73) Assignee: Aortica Corporation, Sunrise, FL (US)

(*) Notice: Subject to any disclaimer, the term of this patent is extended or adjusted under 35 U.S.C. 154(b) by 0 days.

(21) Appl. No.: 16/265,436

(22) Filed: Feb. 1, 2019

(65) Prior Publication Data

US 2019/0388213 A1 Dec. 26, 2019

Related U.S. Application Data

(63) Continuation of application No. PCT/US2017/044822, filed on Aug. 1, 2017.
(Continued)

(51) Int. Cl.
*A61F 2/07* (2013.01)
*A61F 2/954* (2013.01)
(Continued)

(52) U.S. Cl.
CPC ............... *A61F 2/07* (2013.01); *A61F 2/954* (2013.01); *A61F 2/958* (2013.01);
(Continued)

(58) Field of Classification Search
CPC ..................................... A61F 2/07; A61F 2/958
(Continued)

(56) References Cited

U.S. PATENT DOCUMENTS

| 5,123,917 | A | 6/1992 | Lee |
| 5,370,692 | A | 12/1994 | Fink et al. |

(Continued)

FOREIGN PATENT DOCUMENTS

| CN | 104240220 A | 12/2014 |
| EP | 2471498 A1 | 7/2012 |

(Continued)

OTHER PUBLICATIONS

International Search Report and Written Opinion dated Aug. 21, 2017 for International Application No. PCT/US2017/037157, 12 pages.

(Continued)

*Primary Examiner* — Suzette J Gherbi
(74) *Attorney, Agent, or Firm* — Foley Hoag LLP

(57) ABSTRACT

Devices, systems, and methods for coupling a prosthetic implant to a fenestrated body are disclosed herein. In some embodiments, a branch stent graft is provided. The branch stent graft can include an engagement portion for engagement with an opening in a fenestrated body, such as a vessel wall or an aortic stent graft. The engagement portion of the branch stent graft can be coupled to the fenestrated body such that the branch stent graft can move, rotate or shift relative to the fenestrated body but such that axial movement of the branch stent graft is restricted and/or prevented.

16 Claims, 14 Drawing Sheets

Related U.S. Application Data

(60) Provisional application No. 62/369,978, filed on Aug. 2, 2016.

(51) Int. Cl.
*A61F 2/958* (2013.01)
*A61F 2/06* (2013.01)

(52) U.S. Cl.
CPC . *A61F 2002/061* (2013.01); *A61F 2220/0008* (2013.01); *A61F 2220/0075* (2013.01); *A61F 2220/0091* (2013.01); *A61F 2230/001* (2013.01); *A61F 2230/0095* (2013.01); *A61F 2240/002* (2013.01); *A61F 2250/0007* (2013.01); *A61F 2250/0029* (2013.01); *A61F 2250/0039* (2013.01); *A61F 2250/0098* (2013.01)

(58) Field of Classification Search
USPC .................................. 623/1.13–1.23
See application file for complete search history.

(56) References Cited

U.S. PATENT DOCUMENTS

| | | | |
|---|---|---|---|
| 5,507,769 A | 4/1996 | Marin et al. | |
| 5,607,444 A | 3/1997 | Lam | |
| 5,755,769 A | 5/1998 | Richard et al. | |
| 5,984,955 A | 11/1999 | Wisselink | |
| 6,030,414 A | 2/2000 | Taheri | |
| 6,036,702 A | 3/2000 | Bachinski et al. | |
| 6,059,824 A | 5/2000 | Taheri | |
| 6,171,334 B1 | 1/2001 | Cox | |
| 6,280,464 B1 | 8/2001 | Hayashi | |
| 6,395,018 B1 | 5/2002 | Castaneda | |
| 6,524,335 B1 | 2/2003 | Hartley et al. | |
| 6,616,675 B1 | 9/2003 | Evard et al. | |
| 6,719,768 B1 | 4/2004 | Cole et al. | |
| 7,306,623 B2 | 12/2007 | Watson | |
| 7,413,573 B2 | 8/2008 | Hartley et al. | |
| 7,435,253 B1 | 10/2008 | Hartley et al. | |
| 7,833,266 B2 | 11/2010 | Gregorich et al. | |
| 8,172,895 B2 | 5/2012 | Anderson et al. | |
| 8,216,298 B2 | 7/2012 | Wright et al. | |
| 8,236,040 B2 | 8/2012 | Mayberry et al. | |
| 8,249,815 B2 | 8/2012 | Taylor | |
| 8,287,586 B2 | 10/2012 | Schaeffer et al. | |
| 8,337,547 B2* | 12/2012 | Iancea | A61F 2/07 623/1.36 |
| 8,359,118 B2 | 1/2013 | Ono et al. | |
| 8,480,725 B2 | 7/2013 | Rasmussen et al. | |
| 8,641,752 B1 | 2/2014 | Holm et al. | |
| 8,808,351 B2 | 8/2014 | Osborne | |
| 8,897,513 B2 | 11/2014 | Balasubramanian | |
| 8,945,202 B2 | 2/2015 | Mayberry et al. | |
| 8,958,623 B1 | 2/2015 | Grady et al. | |
| 9,095,421 B2 | 8/2015 | Peterson | |
| 9,101,455 B2 | 8/2015 | Roeder et al. | |
| 9,125,733 B2 | 9/2015 | Greenberg et al. | |
| 9,259,336 B2 | 2/2016 | Schaeffer et al. | |
| 9,305,123 B2 | 4/2016 | Leotta et al. | |
| 9,629,686 B2 | 4/2017 | Van Bibber et al. | |
| 9,629,705 B2 | 4/2017 | Douthitt et al. | |
| 9,694,108 B2 | 7/2017 | Cully et al. | |
| 9,724,187 B2* | 8/2017 | Ivancev | A61F 2/07 |
| 9,737,394 B2 | 8/2017 | Coghlan et al. | |
| 9,801,741 B1 | 10/2017 | Thapliyal | |
| 9,861,503 B2 | 1/2018 | Barthold et al. | |
| 10,004,616 B2 | 6/2018 | Chakfe et al. | |
| 10,390,931 B2 | 8/2019 | Douthitt et al. | |
| 10,390,932 B2 | 8/2019 | Lostetter | |
| 10,485,684 B2 | 11/2019 | Marmur et al. | |
| 10,653,484 B2* | 5/2020 | Van Bibber | A61B 34/10 |
| 2002/0042564 A1 | 4/2002 | Cooper et al. | |
| 2002/0042622 A1 | 4/2002 | Vargas et al. | |
| 2002/0062133 A1 | 5/2002 | Gilson et al. | |
| 2002/0095205 A1 | 7/2002 | Edwin et al. | |
| 2002/0188344 A1 | 12/2002 | Bolea et al. | |
| 2002/0193872 A1 | 12/2002 | Trout, III et al. | |
| 2003/0093145 A1 | 5/2003 | Lawrence-Brown et al. | |
| 2004/0034406 A1 | 2/2004 | Thramann | |
| 2004/0059406 A1 | 3/2004 | Cully et al. | |
| 2004/0064081 A1* | 4/2004 | Stanish | A61F 2/06 604/8 |
| 2004/0102866 A1 | 5/2004 | Harris et al. | |
| 2004/0138737 A1 | 7/2004 | Davidson et al. | |
| 2005/0131517 A1 | 6/2005 | Hartley et al. | |
| 2005/0131523 A1 | 6/2005 | Bashiri et al. | |
| 2005/0137518 A1 | 6/2005 | Biggs et al. | |
| 2006/0020319 A1 | 1/2006 | Kim et al. | |
| 2006/0058638 A1 | 3/2006 | Boese et al. | |
| 2006/0116749 A1 | 6/2006 | Willink et al. | |
| 2006/0155359 A1* | 7/2006 | Watson | A61F 2/07 623/1.13 |
| 2006/0259116 A1 | 11/2006 | Feld et al. | |
| 2007/0055360 A1 | 3/2007 | Hanson et al. | |
| 2007/0142900 A1 | 6/2007 | Balaji | |
| 2007/0244547 A1 | 10/2007 | Greenan | |
| 2007/0293936 A1 | 12/2007 | Dobak | |
| 2008/0091260 A1 | 4/2008 | Pomeranz et al. | |
| 2008/0109066 A1 | 5/2008 | Quinn | |
| 2008/0147174 A1 | 6/2008 | Konstantino et al. | |
| 2008/0201007 A1 | 8/2008 | Boyden et al. | |
| 2008/0269867 A1 | 10/2008 | Johnson | |
| 2009/0030502 A1 | 1/2009 | Sun et al. | |
| 2009/0264990 A1 | 10/2009 | Bruszewski et al. | |
| 2009/0304245 A1 | 12/2009 | Egger et al. | |
| 2010/0004730 A1 | 1/2010 | Benjamin et al. | |
| 2010/0063576 A1 | 3/2010 | Schaeffer et al. | |
| 2010/0121429 A1* | 5/2010 | Greenan | A61F 2/07 623/1.15 |
| 2010/0268319 A1 | 10/2010 | Bruszewski et al. | |
| 2011/0054586 A1* | 3/2011 | Mayberry | A61F 2/966 623/1.11 |
| 2011/0060446 A1 | 3/2011 | Ono et al. | |
| 2011/0257720 A1 | 10/2011 | Peterson et al. | |
| 2011/0270378 A1 | 11/2011 | Bruszewski et al. | |
| 2012/0035714 A1 | 2/2012 | Ducke et al. | |
| 2012/0046728 A1 | 2/2012 | Huser et al. | |
| 2013/0116775 A1 | 5/2013 | Roeder et al. | |
| 2013/0123900 A1 | 5/2013 | Eblacas et al. | |
| 2013/0158648 A1 | 6/2013 | Hartley et al. | |
| 2013/0296998 A1 | 11/2013 | Leotta et al. | |
| 2013/0338760 A1 | 12/2013 | Aristizabal et al. | |
| 2014/0046428 A1 | 2/2014 | Cragg et al. | |
| 2014/0180393 A1 | 6/2014 | Roeder | |
| 2014/0277335 A1 | 9/2014 | Greenberg et al. | |
| 2014/0350658 A1 | 11/2014 | Benary et al. | |
| 2015/0005868 A1 | 1/2015 | Koskas et al. | |
| 2015/0073534 A1 | 3/2015 | Roeder et al. | |
| 2015/0105849 A1 | 4/2015 | Cohen et al. | |
| 2015/0202067 A1 | 7/2015 | Barrand et al. | |
| 2015/0209163 A1 | 7/2015 | Kelly | |
| 2015/0216686 A1 | 8/2015 | Chakfe et al. | |
| 2015/0230916 A1* | 8/2015 | Ivancev | A61F 2/95 623/1.13 |
| 2015/0238121 A1 | 8/2015 | Tu et al. | |
| 2015/0313596 A1 | 11/2015 | Todd | |
| 2016/0022450 A1 | 1/2016 | Hehrlein | |
| 2016/0184078 A1 | 6/2016 | Choubey et al. | |
| 2016/0232667 A1 | 8/2016 | Taylor | |
| 2017/0049588 A1 | 2/2017 | Davis et al. | |
| 2017/0112642 A1* | 4/2017 | Hartley | A61F 2/07 |
| 2017/0333133 A1 | 11/2017 | Van Bibber et al. | |
| 2018/0021130 A1 | 1/2018 | Danino | |
| 2018/0064529 A1 | 3/2018 | Sibe | |
| 2018/0116832 A1 | 5/2018 | Pillai | |
| 2018/0153680 A1* | 6/2018 | Greenberg | A61F 2/07 |
| 2018/0228593 A1* | 8/2018 | Eaton | A61F 2/07 |
| 2018/0235787 A1* | 8/2018 | Bolduc | A61F 2/89 |
| 2018/0243076 A1* | 8/2018 | Greenberg | A61F 2/856 |
| 2018/0303641 A1* | 10/2018 | Roeder | A61F 2/915 |
| 2019/0021839 A1* | 1/2019 | Kolbel | A61F 2/89 |
| 2019/0083229 A1* | 3/2019 | Szente Varga | A61F 2/97 |

(56) References Cited

U.S. PATENT DOCUMENTS

| | | | |
|---|---|---|---|
| 2019/0231571 A1 | 8/2019 | Lostetter | |
| 2019/0247178 A1 | 8/2019 | Arbefeuille | |
| 2019/0247179 A1* | 8/2019 | Lostetter | A61F 2/07 |
| 2019/0269497 A1 | 9/2019 | Arbefeuille | |
| 2019/0282355 A1 | 9/2019 | Lostetter | |
| 2019/0328556 A1* | 10/2019 | Eubanks | A61F 2/856 |
| 2019/0336311 A1* | 11/2019 | Schaeffer | A61F 2/915 |
| 2020/0069411 A1* | 3/2020 | Sumanasinghe | A61F 2/07 |
| 2020/0146808 A1* | 5/2020 | Kratzberg | A61F 2/82 |
| 2020/0289256 A1* | 9/2020 | Szente Varga | A61F 2/07 |

FOREIGN PATENT DOCUMENTS

| | | |
|---|---|---|
| EP | 2517672 A1 | 10/2012 |
| EP | 2 606 851 A1 | 6/2013 |
| EP | 2735283 A1 | 5/2014 |
| EP | 2740440 A2 | 6/2014 |
| EP | 2745812 A1 | 6/2014 |
| EP | 2745813 A1 | 6/2014 |
| EP | 2749250 A1 | 7/2014 |
| EP | 2749251 A1 | 7/2014 |
| EP | 3040054 A1 | 7/2016 |
| EP | 3078349 A1 | 10/2016 |
| EP | 3272319 A1 | 1/2018 |
| FR | 2932979 A1 | 1/2010 |
| JP | 2004-529735 A | 9/2004 |
| JP | 2006-500107 A | 1/2006 |
| JP | 2008-526440 A | 7/2008 |
| JP | 2015-527156 A | 9/2015 |
| WO | WO-97/03624 A1 | 2/1997 |
| WO | WO-97/48350 A1 | 12/1997 |
| WO | WO-01/60285 A1 | 8/2001 |
| WO | WO-02/29758 A2 | 4/2002 |
| WO | WO-02/083038 A2 | 10/2002 |
| WO | WO-2005/034809 A1 | 4/2005 |
| WO | WO 2005/034810 A1 | 4/2005 |
| WO | WO-2006/037086 A1 | 4/2006 |
| WO | WO-2007045000 A2 | 4/2007 |
| WO | WO-2008/124222 A1 | 10/2008 |
| WO | WO-2009/148594 A1 | 12/2009 |
| WO | WO 2010/024867 A1 | 3/2010 |
| WO | WO 2010/024880 A1 | 3/2010 |
| WO | WO 2010/030370 A1 | 3/2010 |
| WO | WO 2010/127040 A1 | 11/2010 |
| WO | WO-2012/116368 A2 | 8/2012 |
| WO | WO-2012/145823 A1 | 11/2012 |
| WO | WO-2013066880 A1 | 5/2013 |
| WO | WO 03/099108 A2 | 12/2013 |
| WO | WO-2014/053616 A1 | 4/2014 |
| WO | WO-2015/070792 A1 | 5/2015 |
| WO | WO 2016/098113 A1 | 6/2016 |
| WO | WO 2017/007947 A1 | 1/2017 |
| WO | WO 2017/218474 A1 | 12/2017 |
| WO | WO 2018/026768 A1 | 2/2018 |

OTHER PUBLICATIONS

International Search Report and Written Opinion dated Jan. 4, 2018 for International Application No. PCT/US2017/044822, 15 pages.
International Search Report and Written Opinion dated Apr. 23, 2019 for International Application No. PCT/US2018/052400, 16 pages.
Notice of Reasons for Rejection dated Jan. 14, 2020 for Japanese Application No. 2018-564736, 11 pages.
Chuter et al., "Fenestrated and Branched Stent-Grafts for thoracoabdominal, Pararenal and Juxtarenal Aortic Aneurysm Repair," Seminars in Vascular Surgery, 20:90-96 (2007).
Chuter et al., "Standardized off-the-shelf components for multi-branched endovascular repair of thoracoabdominal aortic aneurysms," Perspectives in Vascular Surgery and Endovascular Therapy, 23(3):195-201 (2011).
Elkouri et al., "Most patients with abdominal aortic aneurysm are not suitable for endovascular repair using currently approved bifurcated stent-grafts," Vascular and Endovascular Surgery, 38(5):401-412 (2004).
Hazer et al., "A workflow for computational fluid dynamics simulations using patient-specific aortic models," 24th CADFEM Users Meeting 2006, International Congress on FEM Technology with 2006 German Ansys Conference, Oct. 25, 2006, 9 pp.
Higashiura et al., "Initial experience of branched endovascular graft for abdominal aortic aneurysm with complex anatomy of proximal neck: planning and technical considerations," Jpn J Radiol, 28:66-74 (2010).
Legget et al., "System for quantitative three-dimensional echocardiography of the left ventricle based on a magnetic-field position and orientation system," IEEE Transactions on Biomedical Engineering, 45(4):494-504 (1998).
Leotta et al., "Measurement of abdominal aortic aneurysms with three-dimensional ultrasound imaging: preliminary report," Journal of Vascular Surgery, 33(4):700-707 (2001).
Malina et al., "EVAR and complex anatomy: an update on fenestrated and branched stent grafts," Scandinavian Journal of Surgery, 97:195-204 (2008).
Nordon et al., "Toward an 'off-the-shelf' fenestrated endograft for management of short-necked abdominal aortic aneurysms: an analysis of current graft morphological diversity," J Endovasc Ther., 17:78-85 (2010).
Oderich et al., "Modified fenestrated stent grafts: device design, modifications, implantation, and current applications," Perspectives in Vascular Surgery and Endovascular Therapy, 21(3):157-167 (2009).
Resch et al., "Incidence and management of complications after branched and fenestrated endographing," Journal of Cardiovascular Surgery, 51(1):105-113 (2010).
Ricotta et al., "Fenestrated and branched stent grafts," Perspective Vascular Surgery and Endovascular Therapy, 20(2):174-187 (2008).
Stratasys, Dimension 1200es 3D modeling printer, Durability Meets Affordability, www.stratasys.com/3d-printers/design-series/performance/dimension-1200es, 2014, 4 pages.
UK Evar Trial Investigators, "Endovascular versus open repair of abdominal aortic aneurysm," New England Journal of Medicine, 362(20):1863-1871 (2010).

* cited by examiner

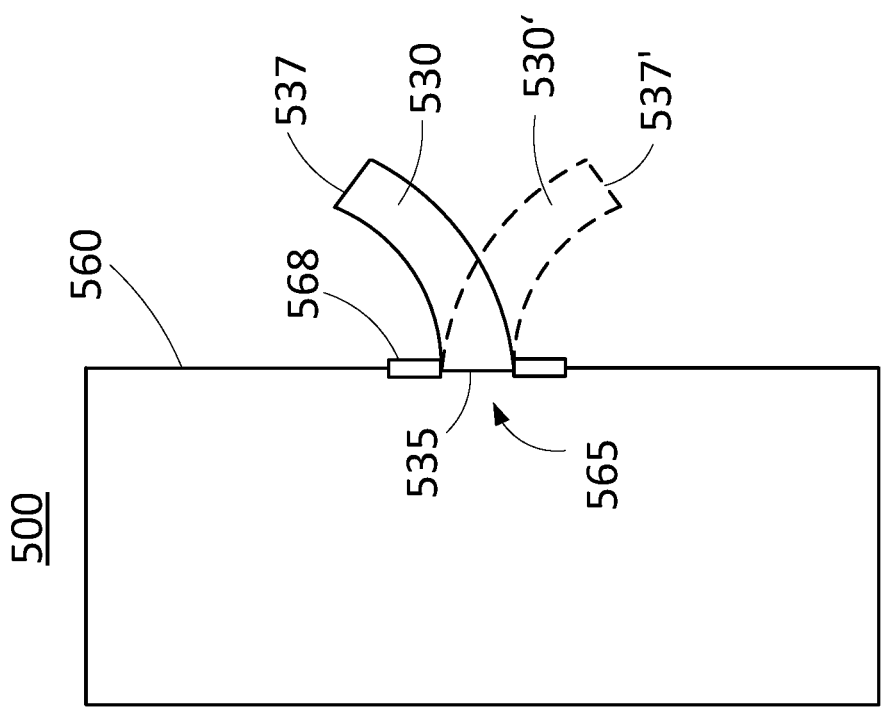

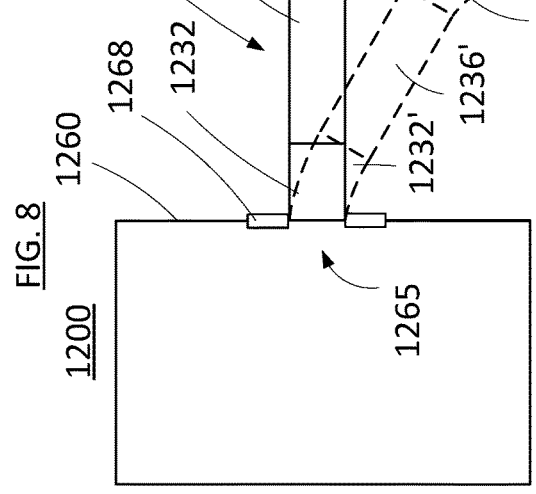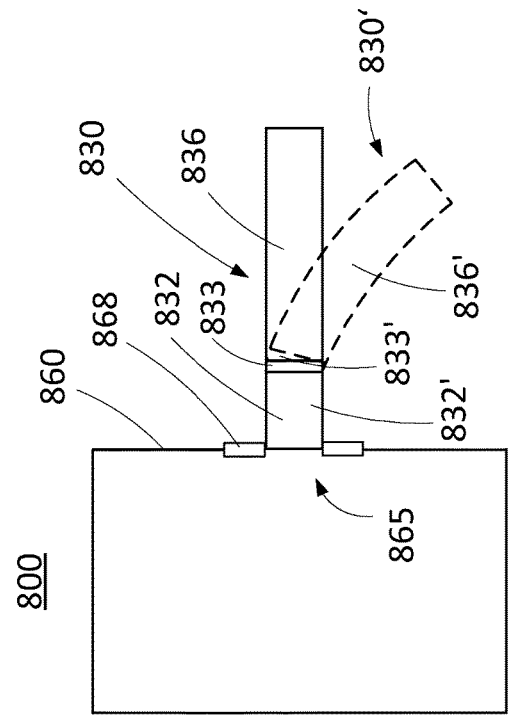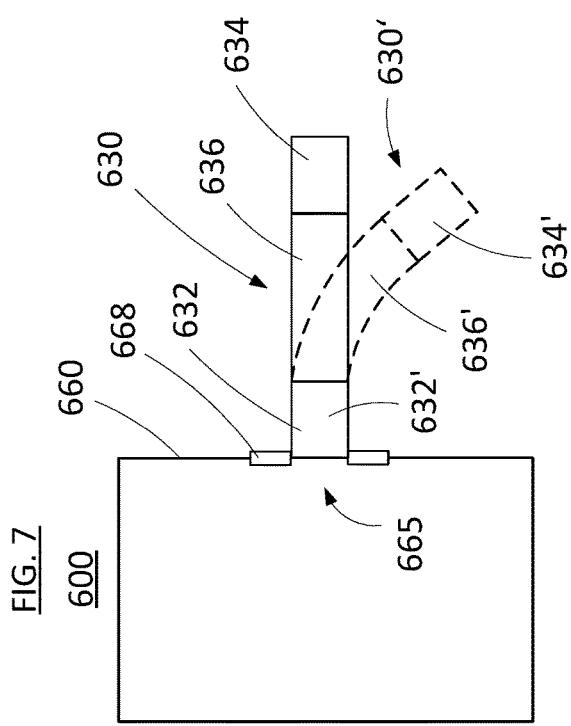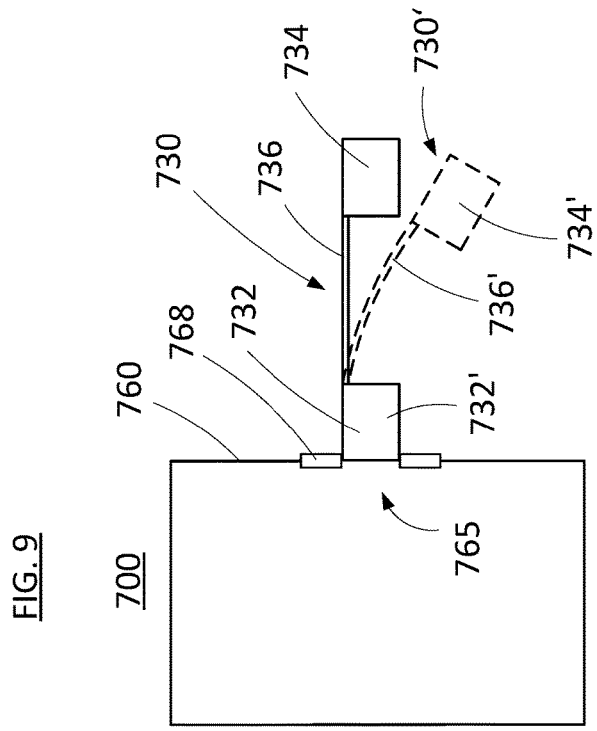

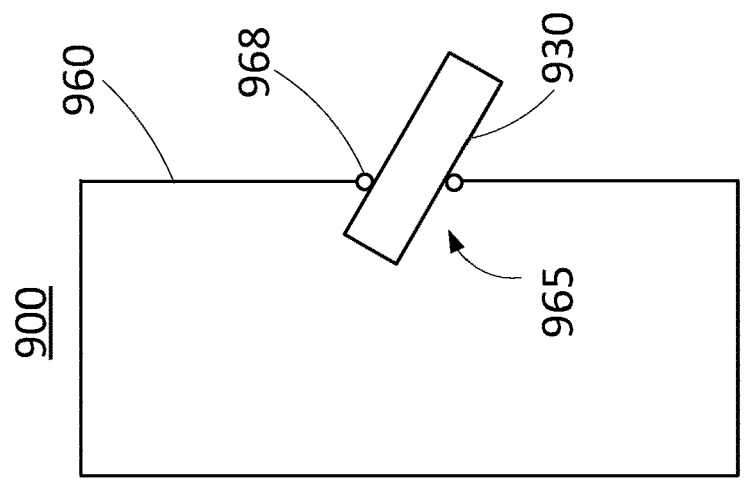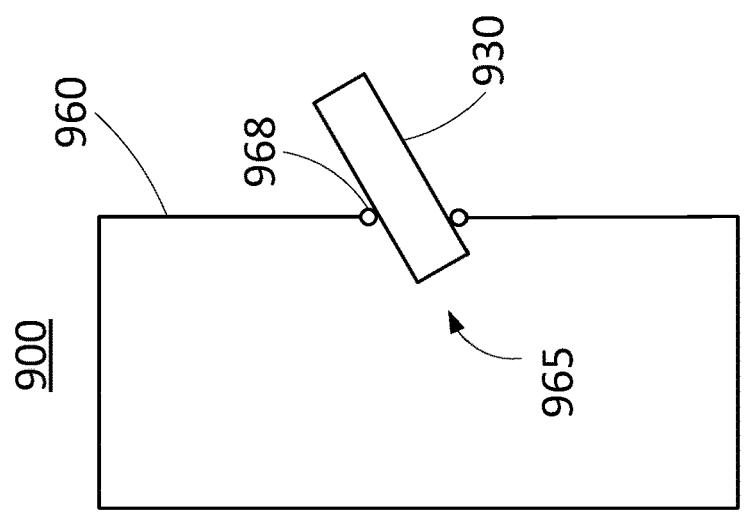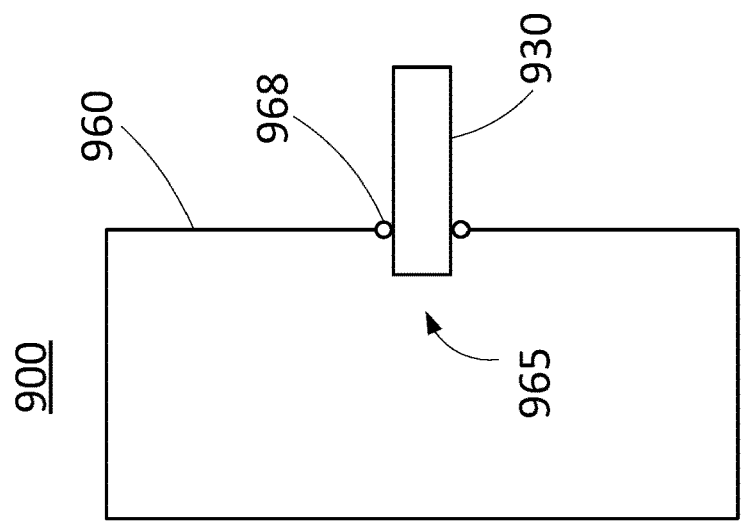

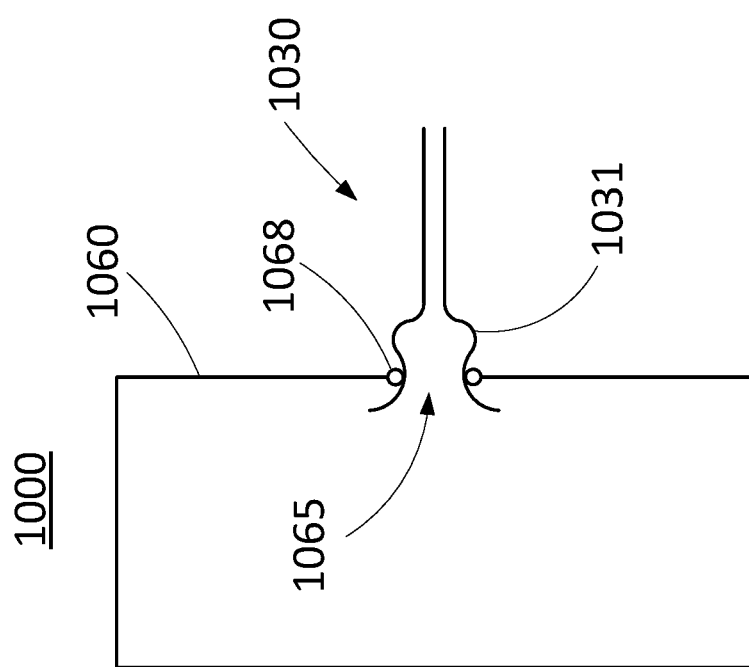

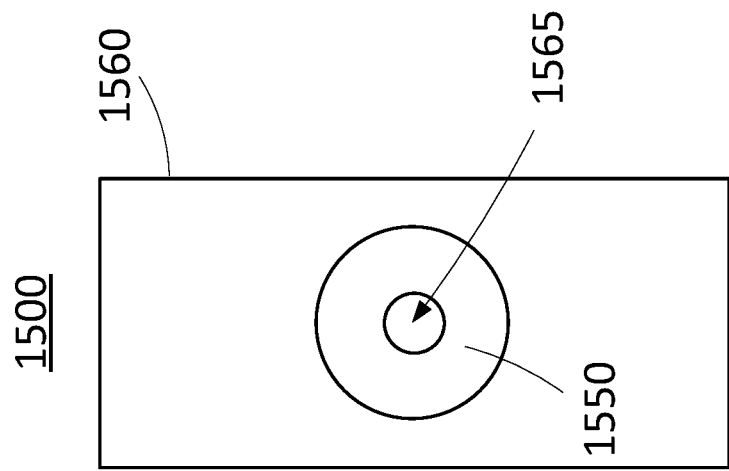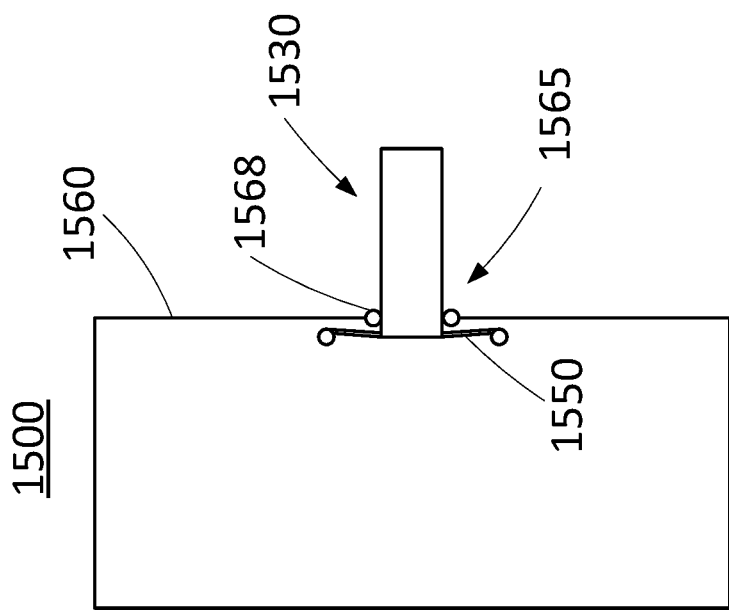

SYSTEMS, DEVICES, AND METHODS FOR COUPLING A PROSTHETIC IMPLANT TO A FENESTRATED BODY

CROSS-REFERENCE TO RELATED APPLICATIONS

This application is a continuation of International Patent Application No. PCT/US2017/044822, filed Aug. 1, 2017 and titled "Systems, Devices, and Methods for Coupling A Prosthetic Implant to a Fenestrated Body," which claims priority to and the benefit of U.S. Provisional Patent Application Ser. No. 62/369,978, entitled "Systems, Devices, and Methods for Coupling a Prosthetic Implant to a Fenestrated Body," filed Aug. 2, 2016, the disclosures of which are hereby incorporated by reference in their entirety.

BACKGROUND

The embodiments described herein relate generally to prosthetic implants and more particularly, to devices and methods for engaging a prosthetic implant, such as, for example, an branch vessel stent graft, within a fenestration of a second prosthetic implant, such as, for example, an aortic stent graft.

Prosthetic devices are often implanted into, for example, diseased portions of a patient to repair, support, stent, and/or otherwise facilitate the proper function of those diseased portions. In some instances, prosthetic devices such as stent grafts can be used to repair diseased portions of a patient's vascular system. For example, aneurysms within a patient's vascular system generally involve the abnormal swelling or dilation of a blood vessel such as an artery, which typically weakens the wall of the blood vessel making it susceptible to rupture. An abdominal aortic aneurysm (AAA) is a common type of aneurysm that poses a serious health threat. A common way to treat AAA and other types of aneurysms is to place an endovascular stent graft in the affected blood vessel such that the stent graft spans across (e.g., traverses) and extends beyond the proximal and distal ends of the diseased portion of the vasculature. The stent graft can, thus, reline the diseased vasculature, providing an alternate blood conduit that isolates the aneurysm from the high-pressure flow of blood, thereby reducing or eliminating the risk of rupture. In other instances, a prosthetic device can be an implant and/or mechanism, which can provide structural or functional support to a diseased and/or defective portion of the body. In some instances, however, the arrangement of the anatomy can present challenges when attempting to place and/or secure a prosthetic device (including stent grafts or the like). Such challenges can result in misalignment and/or suboptimal configuration of the prosthetic device within the anatomy.

Minimally invasive endovascular repair using stent grafts is often preferred to avoid the risks associated with traditional open surgical repair. However, these stent grafts can only be used when the graft can be placed in a stable position without covering major branch vessels. In the cases of juxtarenal aneurysm where the dilation extends up to but does not involve the renal arteries, the proximal portion of the stent graft needs to be secured to the aortic wall above the renal arteries, thereby blocking the openings to the renal arteries. Thus, patients with juxtarenal aneurysms, which represent a significant proportion of abdominal aortic aneurysm cases, are typically excluded from endovascular treatment.

To allow for endovascular repair of a wider range of cases, surgeons sometimes cut openings in the stent graft body to accommodate specific branch vessel origins, a process known as "fenestration". Thus, for example, in treating juxtarenal aneurysms using a procedure known as Fenestrated Endovascular Aortic Repair ("FEVAR"), the fenestrations or openings of an aortic stent graft are to be aligned with the branch vessels. Additional stent grafts (e.g., renal stents) can then be placed in the branch vessels and secured to the primary stent graft (e.g., aortic stent graft) to limit movement of the primary stent grafts within the anatomy and ensure proper blood flow. Additionally, in some cases, an endovascular stent graft can be placed within one or more specific branch vessels to further treat an aneurysm and/or to reinforce the branch vessel in the region of the aneurysm.

SUMMARY

Devices, systems, and methods for coupling a prosthetic implant to a fenestrated body are disclosed herein. In some embodiments, a branch stent graft is provided. The branch stent graft can include an engagement portion for engagement with an opening in a fenestrated body, such as a vessel wall or an aortic stent graft. The engagement portion of the branch stent graft can be coupled to the fenestrated body such that the branch stent graft can rotate or shift relative to the fenestrated body but such that axial movement of the branch stent graft is restricted and/or prevented.

BRIEF DESCRIPTION OF THE DRAWINGS

FIG. 6 is a schematic illustration of a cross-sectional side view of a system, according to an embodiment.

FIG. 7 is a schematic illustration of a cross-sectional side view of a system, according to an embodiment.

FIG. 8 is a schematic illustration of a cross-sectional side view of a system, according to an embodiment.

FIG. 9 is a schematic illustration of a cross-sectional side view of a system, according to an embodiment.

FIG. 10 is a schematic illustration of a cross-sectional side view of a system, according to an embodiment.

FIGS. 11A-11C are schematic illustrations of cross-sectional side views of a system in a first configuration, a second configuration, and a third configuration, respectively, according to an embodiment.

FIG. 12 is a schematic illustration of a cross-sectional side view of a system, according to an embodiment.

FIG. 16D is a schematic illustration of a cross-sectional side view of the system of FIG. 16A in a fourth configuration.

FIG. 16E is a schematic illustration of an internal wall of the system of 16D in the second configuration.

DETAILED DESCRIPTION

Figure 1:
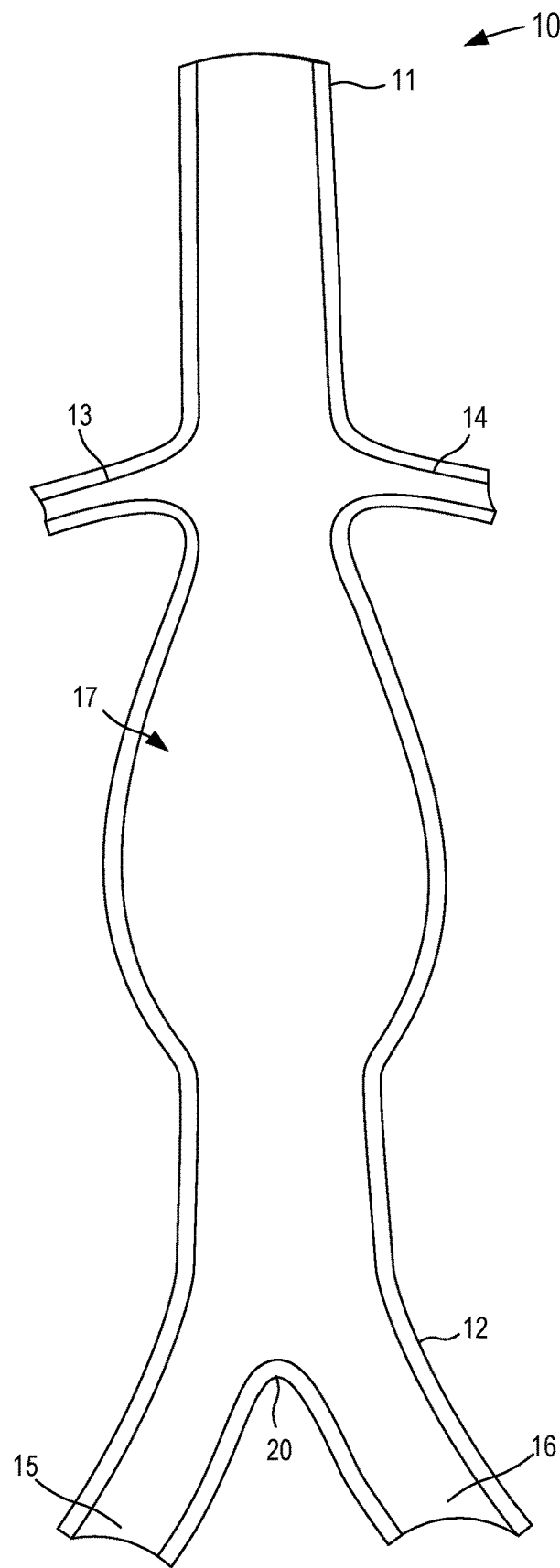
FIG. 1 is an illustration of a diseased abdominal aorta according to an embodiment.

Devices, systems, and methods for coupling a prosthetic implant to a fenestrated body are disclosed herein. In some embodiments, a fenestrated body includes a flexible engagement portion. The prosthetic implant can be configured to engage with the flexible engagement portion such that the prosthetic implant can rotate relative to the fenestrated body while maintaining a perpendicular angle between a longitudinal central axis of the prosthetic implant and a plane of the flexible engagement portion.

In some embodiments, a branch stent graft is provided. The branch stent graft can include an engagement portion for engagement with an opening in a fenestrated body, such as a vessel wall or an aortic stent graft. The engagement portion of the branch stent graft can be coupled to the fenestrated body such that the branch stent graft can rotate or shift relative to the fenestrated body but such that axial movement of the branch stent graft is restricted and/or prevented.

As used in this specification, the singular forms "a," "an" and "the" include plural referents unless the context clearly dictates otherwise. Thus, for example, the term "a member" is intended to mean a single member or a combination of members, "a material" is intended to mean one or more materials, or a combination thereof.

As used herein, the words "proximal" and "distal" refer to a direction closer to and away from, respectively, an operator of, for example, a medical device. Thus, for example, the end of the medical device contacting the patient's body would be the distal end of the medical device, while the end opposite the distal end would be the proximal end of the medical device. Similarly, when a device such as an endovascular stent graft is disposed within a portion of the patient, the end of the device closer to the patient's heart would be the proximal end, while the end opposite the proximal end would be the distal end. In other words, the proximal end of such a device can be upstream of the distal end of the device.

The embodiments described herein can be formed or constructed of one or more biocompatible materials. Examples of suitable biocompatible materials include metals, ceramics, or polymers. Examples of suitable metals include pharmaceutical grade stainless steel, gold, titanium, tungsten, nickel, iron, platinum, tin, chromium, copper, and/or alloys thereof. Examples of polymers include nylons, polyesters, polycarbonates, polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, polyethylene terephthalate (PET), polytetrafluoroethylene (PTFE), urethanes, and/or blends and copolymers thereof.

The embodiments and methods described herein can be used to form a patient-specific prosthetic device and/or to facilitate the function and/or the integration of the prosthetic device within a portion of a patient. For example, in some embodiments, the devices and/or methods described herein can be used in conjunction with and/or can otherwise be included in endovascular repair using stent grafts. Although the embodiments are shown and described herein as being used, for example, to facilitate endovascular repair, in other embodiments, any of the devices and/or methods described herein can be used to facilitate treatment of any portion of a patient. For example, the devices and methods described herein can form and/or can facilitate the integration of any suitable implant, prosthesis, device, mechanism, machine, and/or the like within a portion of the body of a patient such as the patient's vascular system, nervous system, muscular-skeletal system, etc. Therefore, while some embodiments are shown and described herein as being used in the endovascular repair of an abdominal aortic aneurysm, they are presented by way of example and are not limited thereto.

Some of the devices and/or methods described herein can be used in minimally invasive treatment techniques such as endovascular repair using stent grafts. Such repair techniques are generally preferred over traditional open surgical repair and often result in reduced morbidity or mortality rates. In some instances, however, the arrangement of the diseased vasculature can result in a need to alter a portion of the stent graft prior to insertion into the body. For example, in an endovascular repair of an abdominal aortic aneurysm, the aneurysm can be situated adjacent to and/or directly distal to normally functioning vessels branching from a portion of the aorta. In order to reline the aneurysm with the stent graft, surgeons often cut openings in the stent graft fabric to accommodate specific branch vessel origins, a process known as "fenestration." Specifically, in treating juxtarenal aneurysms and/or when treating other aneurysms, shown in illustration in FIG. 1 for instance, the fenestrations or openings of the stent grafts can correspond to a size, shape, and/or relative position of, inter alia, the renal arteries, the superior mesenteric artery (SMA), and/or the celiac artery (not shown in the illustration in FIG. 1).

Traditionally, the fenestration process involves measurements based on medical images (such as CT scans) of the vessel origins. For example, in some instances, longitudinal distances of branch vessels can be measured and relative angular locations of the branch vessels can be estimated and/or calculated from a reference point. Based on these measurements and/or calculations, a surgeon or manufacturer can mark and cut the stent fabric of a stent graft to define one or more fenestrations. The fenestrated stent graft can then be positioned within the diseased vasculature (e.g., via an endovascular procedure) and oriented to substantially align the fenestrations with openings of the corresponding branch vessels.

In some instances, fenestrations in the fenestrated bodies (e.g., fenestrated stent grafts or vessel walls) described herein can be generated and/or otherwise formed based on medical imaging data of a diseased portion of a patient's vascular system (e.g., an abdominal aortic aneurysm). For example, an electronic device such as a personal computer, workstation, laptop, etc. can receive the imaging data and can calculate and/or otherwise define a digital representation of the imaging data. Based on the digital representation, the electronic device can define one or more templates, process plans, instructions, data sets, and/or the like associated with and/or indicative of a desired set of fenestration locations along a body (e.g., a stent graft). In some instances, the electronic device can output a map, plan, and/or template, which in turn, can be used by a doctor, surgeon, technician, and/or manufacturer to form a fenestrated body (e.g. a fenestrated stent graft). For example, in some embodiments, such a template or the like can be substantially similar to those described in U.S. Patent Publication No. 2013/0296998 entitled, "Fenestration Template for Endovascular Repair of Aortic Aneurysms," filed May 1, 2013 ("the '998 publication") and/or those described in U.S. patent application Ser. No. 15/163,255 entitled, "Devices and Methods for Anatomic Mapping for Prosthetic Implants," filed May 24, 2016 ("the '255 application"), the disclosures of which are incorporated herein by reference in their entireties.

In other instances, fenestrations in the fenestrated bodies (e.g. a fenestrated stent grafts or vessel walls) can be formed without such templates. For example, in some embodiments, the electronic device can output instructions and/or code (e.g., machine code such as G-code or the like) to a computerized numerical control (CNC) device and/or a computer-aided manufacturing (CAM) device, which in turn, can perform one or more manufacturing processes or the like associated with forming and/or otherwise marking fenestration locations along a patient-specific prosthesis (e.g., a stent graft). The formation of a patient-specific prosthesis can be performed in a manual process or in at least a partially automated process. Moreover, a change in the arrangement of a portion of the anatomy resulting from the insertion and/or indwelling of the prosthesis can be determined and/or calculated using the devices and/or methods described in International Patent Application No. PCT/US2016/041355, entitled "Devices and Methods for Anatomic Mapping for Prosthetic Implants," filed Jul. 7, 2016 ("the '355 application"), the disclosure of which is incorporated herein by reference in its entirety.

Figure 2A:
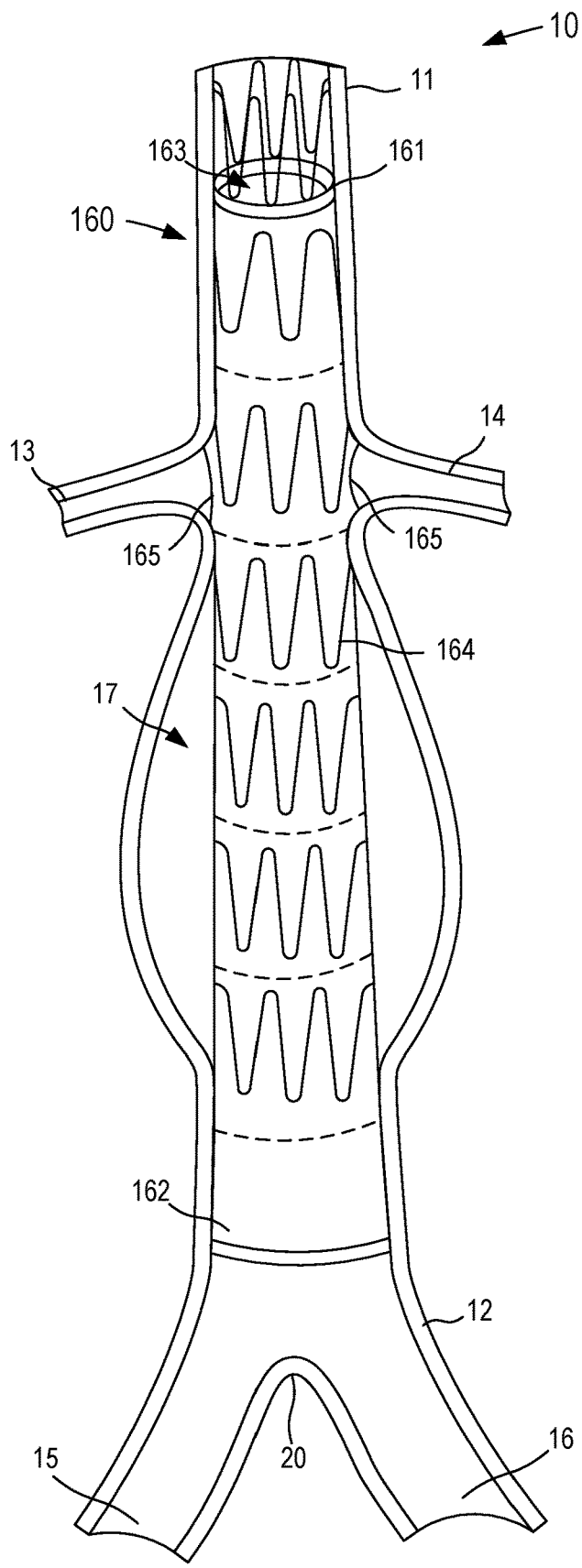
FIG. 2A is a portion of a stent graft according to an embodiment and directly after placement within the diseased abdominal aorta of FIG. 1.
Figure 2B:
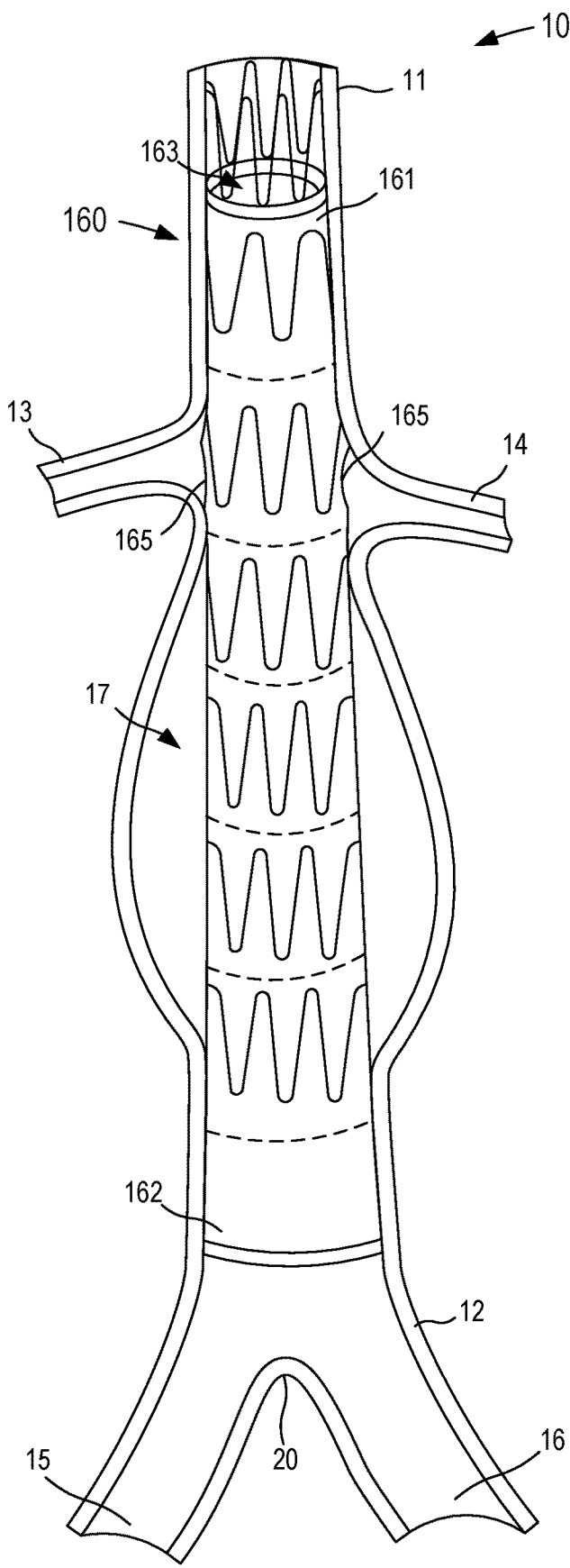
FIG. 2B is a portion of the stent graft of FIG. 2A and placed within the diseased abdominal aorta of FIG. 1 and after a time of indwelling.

FIGS. 1-2B illustrate a diseased portion of a patient's abdominal aorta 10. While portions of the abdominal aorta 10 are described below, the discussion of the abdominal aorta 10 is not exhaustive; rather, the discussion below provides a reference to the relevant anatomic structures. Moreover, the discussion of the anatomic structures (e.g., of the abdominal aorta 10) refers to the position, orientation, etc. of such structures relative to the patient rather than as viewed by an observer (e.g., a doctor). For example, when referring to a "left" side of a patient or to anatomic structures disposed on or near the "left" side of the patient, "left" is intended to describe a position relative to the patient and/or from the patient's perspective, as viewed in an anterior direction (e.g., forward).

The abdominal aorta 10 (also referred to herein as "aorta") has a proximal end portion 11, receiving a flow of blood from the descending aorta (not shown), and a distal end portion 12, supplying a flow of blood to the lower limbs. As shown in FIG. 1, the aorta 10 at or near the proximal end portion 11 supplies a flow of blood to the right renal artery 13 and the left renal artery 14, which in turn, supply blood to the right and left kidney (not shown), respectively. Although not shown in FIG. 1, the proximal end portion 11 of the aorta 10 also supplies a flow of blood to the superior mesenteric artery (SMA) and the celiac artery. The distal end portion 12 of the aorta 10 forms the iliac bifurcation 20, through which the aorta 10 supplies a flow of blood to the right common iliac artery 15 and the left common iliac artery 16, which in turn, supply blood to the right and left lower limbs, respectively. As shown in FIG. 1, this patient has an abdominal aortic aneurysm (AAA) 17 positioned distal to the renal arteries 13 and 14 and proximal to the iliac bifurcation 20. More specifically, the AAA 17 is disposed in a position that precludes the attachment of a proximal end portion of a stent graft between the renal arteries 13 and 14 and the AAA 17, and thus, a fenestrated stent graft 160 (se e.g., FIGS. 2A and 2B) is used for endovascular repair of the AAA 17.

In some instances, endovascular repair of the AAA 17 includes scanning and/or otherwise capturing anatomic imaging data associated with the patient's aorta 10. For example, an imaging device can be an X-ray device, a computed tomography (CT) device, a computed axial tomography (CAT) device, a magnetic resonance imaging device (MRI), a magnetic resonance angiogram (MRA) device, a positron emission tomography (PET) device, a single photon emission computed tomography (SPECT) device, an ultrasound device, and/or any other suitable device for imaging a portion of the patient and/or a combination thereof (e.g., a CT/MRA device, a PET/CT device, a SPECT/CT device, etc.). The imaging data captured by the imaging device can thus, be used to determine salient features of the patient's aorta 10 such as, for example, the branch vessels in fluid communication with the aorta 10. For example, a doctor, surgeon, technician, manufacturer, etc. can use the imaging data to determine and/or calculate a size, shape, position, and/or orientation of the aorta 10, the branch vasculature in fluid communication with the aorta 10 (e.g., the renal arteries 13 and 14), and/or any other suitable vasculature or anatomic structure. In some instances, the doctor, surgeon, technician, manufacturer, etc. can form and/or define one or more fenestrations 165 in the stent graft 160 associated with the determined and/or calculated characteristics of at least the renal arteries 13 and 14, as described in the '998 application, the '255 application, and/or the '355 application, incorporated by reference above.

As shown in FIG. 2A, the stent graft 160 can be positioned within a portion of the patient's abdominal aorta 10 via an endovascular procedure. For example, the stent graft 160 can be disposed within a delivery catheter (e.g., in a collapsed, compressed, restrained, and/or otherwise un-deployed configuration), which is inserted into, for example, the femoral artery (not shown). The delivery catheter can be advanced through the artery and into the abdominal aorta 10. Once advanced to a desired position within the abdominal aorta 10, the delivery catheter can be withdrawn relative to the stent graft 160. As the delivery catheter is retracted and/or withdrawn, the stent graft 160 transitions from the collapsed configuration to an expanded or deployed configuration, thereby stenting a portion of the abdominal aorta 10.

The stent graft 160 includes a proximal end portion 161 and a distal end portion 162 and defines a lumen therethrough 163. The stent graft 160 can be any suitable stent graft. For example, the stent graft 160 can be formed from a resilient, biocompatible material such as those described above. For example, a stent graft can include a stent or framework to which a graft material is coupled. In some embodiments, the stent (i.e., framework) can be constructed from a metal or metal alloy such as, for example, nickel titanium (nitinol) and the graft material can be constructed from a woven polymer or fabric such as, for example, polytetrafluoroethylene (PTFE) or polyethylene terephthalate (PET or Dacron®)). In some embodiments, the graft material or fabric can be woven onto the stent and/or coupled to the stent in any other suitable manner to form the stent graft (e.g., the stent graft 160).

The stent graft 160 also includes a set of stiffening members 164 disposed circumferentially about the stent graft 160. The stiffening members 164 can be any suitable structure that can, for example, bias the stent graft 160 in an open configuration, thereby structurally supporting the stent graft material (also known as "stent fabric" or "graft fabric"). In some embodiments, the stiffening members 164 can be formed from a metal or a metal alloy such as, for example, those described above. In some embodiments, such a metal or metal alloy, for example, is radiopaque and/or otherwise coated with a radiopaque material configured to be visible using, for example, fluoroscopy. The stiffening members 164 can transition from a restrained or deformed delivery configuration (e.g., when disposed in a delivery catheter) to an expanded and/or biased indwelling configuration, as shown in FIG. 2A.

In this embodiment, the stent graft 160 defines the set of fenestrations 165, as described above. As described herein, the position of the fenestrations 165 along the stent graft 160 can be based on anatomic imaging data and/or one or more digital representations of the patient's anatomy. A doctor, surgeon, technician, and/or manufacturer can then use the imaging data and/or digital representations to define the fenestrations 165 in the graft fabric. As shown, in this example, the fenestrations 165 are each aligned with its corresponding renal artery 13 or 14 and can each have a size, shape, and/or configuration that is associated with its corresponding renal artery 13 or 14. In this manner, the fenestrations 165 can allow blood to flow from the aorta 10 and into the right renal artery 13 and the left renal artery 14 via the fenestrations 165. Although not shown in FIG. 2A, the stent graft 160 can define one or more fenestrations associated with other branch vessels stemming from the aorta 10 such as, for example, the superior mesenteric artery (SMA), the celiac artery, and/or the like.

As shown in FIG. 2B, the placement and/or indwelling of the stent graft 160 within the aorta 10 can, for example, alter, shift, rotate, translate, morph, and/or otherwise reconfigure the arrangement of the patient's aorta 10. As a result, the openings of the renal arteries 13 and 14 are shifted relative to the fenestrations 165 defined by the stent graft 160. In some instances, the shifting of the aorta 10 relative to the stent graft 160 results in at least a partial blockage of the renal arteries 13 and 14, as shown in FIG. 2B. For example, in some instances, the openings of the renal arteries 13 and 14 can be about 4 millimeters (mm) to about 7 mm, and the shifting and/or rearrangement of the aorta 10 can result in a shifting of the openings of the renal arteries 13 and 14 relative to the fenestrations 165 by about 1 mm, about 2 mm, about 3 mm, about 4 mm, about 5 mm, about 6 mm, about 7 mm, or more (or fraction of a millimeter there between). Thus, despite defining the fenestrations 165 in desired positions along the stent graft 160 based on the imaging data, the shifting of the aorta 10 resulting from the placement and/or indwelling of the stent graft 160 can result in a blockage of the renal arteries 13 and 14. In some instances, the shifting of the aorta 10 can result in about a 1%, 5%, 10%, 20%, 30%, 40%, 50%, 60%, 70%, 80%, 90%, or 100% (or any percent or fraction of a percent there between) blockage of the renal arteries 13 and 14. Although not shown in FIGS. 2A and 2B, the shifting of the aorta 10 can result in a similar misalignment of any branch vessel relative to its corresponding fenestration in the stent graft 160. In some embodiments, an electronic device can be configured to determine and/or calculate the shift in the anatomy that would result from the insertion and/or indwelling of prosthesis (e.g., a stent graft) and can define one or more digital representations of the shifted anatomy. One or more fenestrations can be formed in a stent graft (e.g., the stent graft 160) based on the calculated shift, as described in the '998 application, the '255 application, and/or the '355 application, incorporated by reference above.

Figure 3:
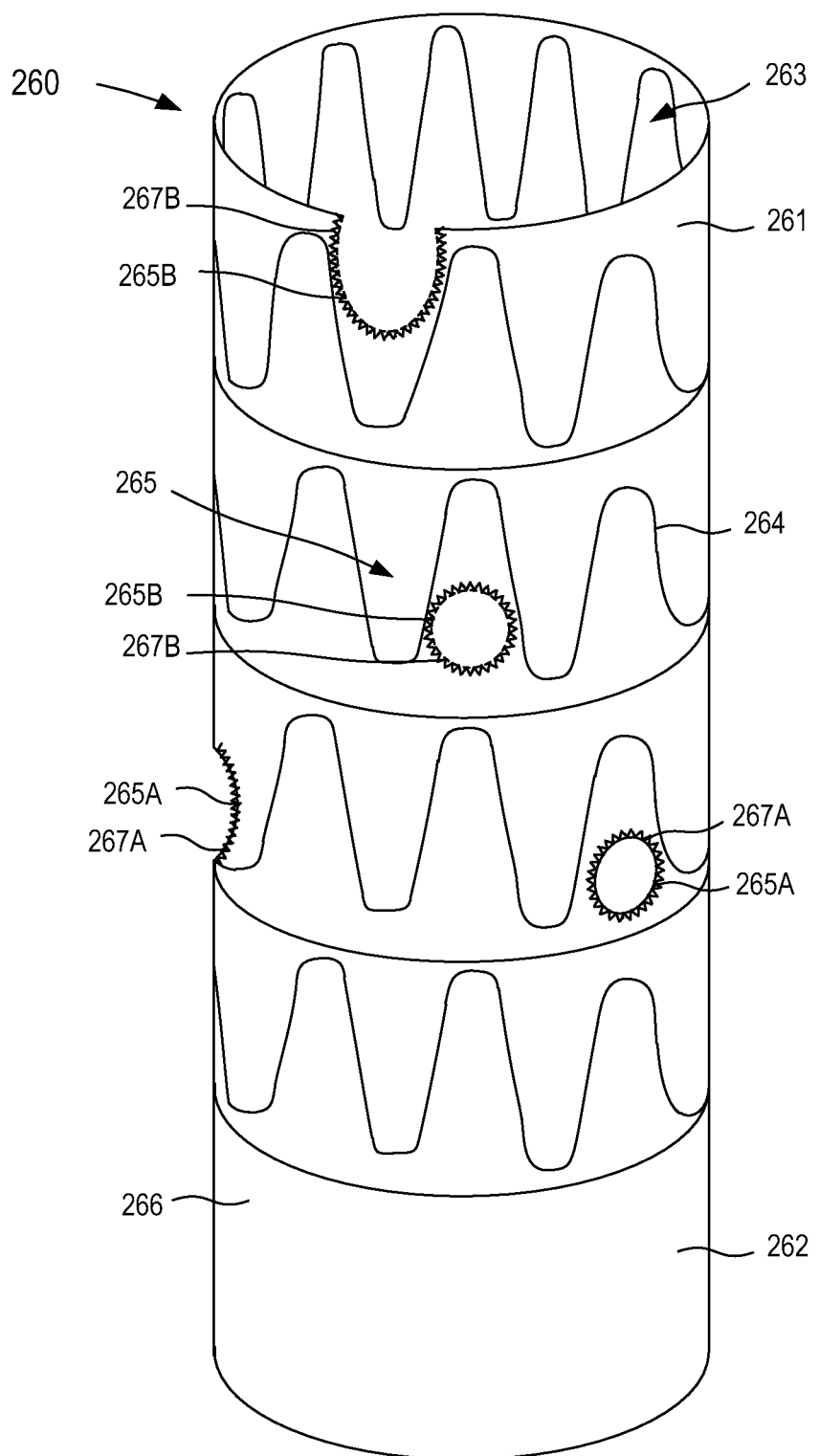
FIG. 3 is an illustration of at least a portion of a fenestrated stent graft according to an embodiment.

FIG. 3 illustrates at least a portion of a fenestrated stent graft 260 according to an embodiment. As described above, a stent graft can define one or more fenestrations configured to accommodate one or more branch vessels when the stent graft is deployed in an aorta. Specifically, in this embodiment, the fenestrated stent graft 260 includes a proximal end portion 261 and a distal end portion 262, and defines a lumen 263 and a set of fenestrations 265. The fenestrated stent graft 260 can be any suitable stent graft and/or prosthesis. For example, in some embodiments, the fenestrated stent graft 260 can be an off-the-shelf stent graft. In other embodiments, the fenestrated stent graft 260 can be a patient-specific stent graft with a size, shape, and/or configuration corresponding to the patient's anatomy.

The fenestrated stent graft 260 (also referred to herein as "stent graft") can have any suitable shape, size, and/or configuration. For example, in some embodiments, the stent graft 260 can have a size that is associated with a size of the lumen defined by the aorta. In other embodiments, the fenestrated stent graft 260 can have a size that is associated with an adjusted or calculated size of the lumen defined by the aorta resulting from the endovascular placement of the stent graft 260. Moreover, the stent graft 260 can have any suitable mechanical properties such as, for example, strength, stiffness, etc.

As shown in FIG. 3, in some embodiments, the stent graft 260 can include stent 264 and a graft fabric 266. The stent 264 can be, for example, any suitable stent and/or framework configured to increase a stiffness of the stent graft 260 and/or to provide structural support for the stent graft 260. As described above, the stent 264 can be formed from any suitable metal or metal alloy such as nitinol. In some embodiments, the stent 264 can be configured to transition between a first, expanded and/or implanted configuration and a second, collapsed, and/or delivery configuration. Furthermore, in some instances, the stent 264 can be biased such that the stent 264 is in the first configuration until a force is exerted on the stent 264 to transition it from the first configuration to the second configuration (e.g., when disposed in a delivery cannula or the like).

The graft fabric 266 can be formed from any suitable polymer or fabric such as, for example. Dacron® or the like. In some embodiments, the graft fabric 266 can be woven around and/or through the stent 264. In other embodiments, the graft fabric 266 can be coupled to the stent 264 via sutures, a friction fit, or an adhesive, and/or can encapsulate the stent 264 between at least two layers of graft fabric 266. As shown in FIG. 3, the graft fabric 266 defines the fenestrations 265, which can be arranged relative to the stent 264 such that the fenestrations 265 do not overlap the stent 264. In other words, the fenestrations 265 can be arranged along the stent graft 260 such that one or more portions of the stent 264 do not span and/or otherwise traverse the fenestrations 265. In other embodiments, one or more portions of the stent 264 can span and/or otherwise traverse the fenestration 265. Moreover, as described in detail above, the fenestrations 265 can be defined by the graft fabric 266 at locations along the stent graft 260 based on an updated, projected, anticipated, and/or otherwise calculated digital representation of a portion of a patient's vasculature.

As described above, the stent graft 260 can be any suitable stent graft and can be formed via any suitable manufacturing process or processes. In some embodiments, the stent graft 260 can be manufactured as an off-the-shelf stent graft and the fenestrations 265 can be formed in the graft material 266 in a subsequent manufacturing process. In other embodiments, the stent graft 260 can be manufactured as a "custom" or not-off-the-shelf stent graft. While specific methods of manufacturing are described herein, it is to be understood that the methods are presented by way of example only and not limitation. Moreover, the methods of manufacturing described herein can be performed at a single facility and/or in a single manufacturing process or can be performed at multiple facilities and/or in multiple manufacturing processes. In some instances, portions of the methods of manufacturing described herein can be performed by an end user such as a doctor, surgeon, technician, nurse, etc. Thus, while the manufacturing of the stent graft 260 is specifically described below, the stent graft 260 can be formed via any suitable manufacturing process or processes and is not limited to those discussed herein.

In some instances, the stent graft 260 can be manufactured with a general shape, diameter, length, etc. associated with a patient's aorta based on, for example, calculations from anatomic imaging data of the patient. In other embodiments, the stent graft 260 can have a general shape, size, and/or configuration associated with the updated model defined by the electronic device, which in turn, corresponds to a calculated, projected, and/or modified arrangement of the aorta in response to the insertion and indwelling of, for example, the stent graft 260, as described in detail above. Hence, a stent graft 260 generally has a tubular or cylindrical shape. In some embodiments, the diameter of the lumen 263 is at least partially based on a diameter of the calculated, projected, and/or modified lumen defined by the aorta. Moreover, the stent graft 260 can have a stiffness and/or any other suitable mechanical properties associated with an anticipated amount and/or method of shifting of the aorta resulting from the insertion and/or indwelling of the stent graft 260, as described in the '998 application, the '255 application, and/or the '355 application, incorporated by reference above.

The fenestrations 265 can be defined along the stent graft 260 such that each fenestration 265 corresponds to a calculated position of the corresponding branch vasculature such as, for example, the renal arteries, and each fenestration 265 can be formed in any suitable manner, as described in the '998 application, the '255 application, and/or the '355 application, incorporated by reference above.

Figure 4:
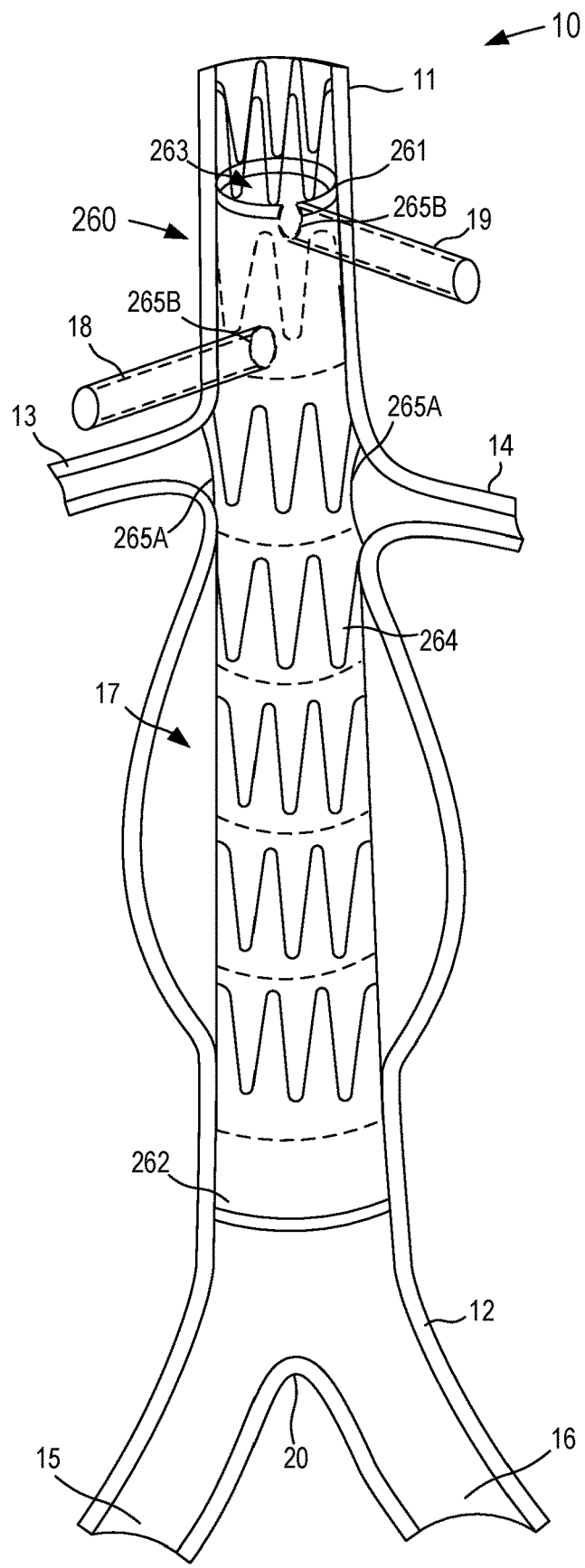
FIG. 4 is an illustration of the portion of the fenestrated stent graft of FIG. 3 positioned, for example, within a portion of a diseased abdominal aorta.

As shown in FIG. 4, when the fenestrations 265 are defined along the stent graft 260, the stent graft 260 can be positioned within a portion of the patient's body using any suitable endovascular procedure. In this embodiment, the stent graft 260 is positioned within the patient's aorta 10. As shown, the stent graft 260 can include, for example, a first set of fenestrations 265A, which are associated with and/or otherwise correspond to the right renal artery 13 and the left renal artery 14. Specifically, each of the fenestrations 265A are aligned with its corresponding renal artery 13 or 14 and can each have a size, shape, and/or configuration that is associated with its corresponding renal artery 13 or 14. In some embodiments, the size, shape, and/or position of the fenestrations 265A is associated with and/or substantially corresponds to the adjusted and/or calculated size, shape, and/or position of its corresponding renal artery 13 and 14. For example, placing the stent graft 260 within the aorta 10 can, for example, alter, shift, rotate, translate, morph, and/or otherwise reconfigure the arrangement of the patient's aorta 10. Thus, by basing the stent graft 260 off of the updated model, the size, shape, and/or position of the fenestrations 265 defined by the stent graft 260 can correspond to the desired branch vasculature (e.g., the right renal artery 13 and/or the left renal artery 14). Moreover, in addition to positioning the stent graft 260 within a portion of the patient's aorta 10, the renal arteries 13 and/or 14 can also be stented, for example, through the fenestrations 265A (not shown in FIG. 4). Stenting of the renal arteries can be carried out with secondary branch stents (not shown in FIG. 4) that engage with the fenestrated body of the stent graft 260 at the fenestrations 265A and extend within branch arteries like the renal arteries 13 and/or 14. As such, the fenestrations 265A on the stent graft 260 and the secondary branch stents (not shown) positioned to correspond to the branch arteries can help with the axial and/or radial alignment and positioning of the stent graft 260 during deployment. Further the fenestrations 265A and the secondary branch stents (not shown) can also help maintain the alignment and positioning of the stent graft 260 relative to the patient's aorta 10 after placement.

As shown in FIGS. 3 and 4, in some embodiments, the stent graft 260 can include a second set of fenestrations 265B, which are associated with and/or otherwise correspond to other branch vessels that otherwise, might be blocked by an un-fenestrated portion of the stent graft 260. For example, the fenestrations 265B can be associated with and/or otherwise correspond to the superior mesenteric artery (SMA) 18 and the celiac artery 19, respectively. In other embodiments, the stent graft 260 can define fenestrations to accommodate more or fewer branch vessels than illustrated here. For example, in some embodiments, the stent graft 260 can define fenestrations to accommodate the inferior mesenteric artery (IMA), internal iliac arteries, and/or the like. Thus, the fenestrations 265 defined by the stent graft 260 can allow blood to flow from the aorta 10 to the branch vasculature, which would otherwise be obstructed by the stent graft 260 material.

In some embodiments, the arrangement of the stent graft 260 and/or the patient's aorta can be such that a fenestration 265 is partially defined by the stent graft 260. For example, as shown, the proximal most fenestration 265B is disposed at the proximal end of the stent graft 260 and corresponds to the celiac artery 19 that is partially covered by the graft material during deployment. As such, the fenestration 265B for the celiac artery 19 is partially circular or U-shaped to accommodate the portion of the celiac artery 19 otherwise blocked by the graft material. In other embodiments, any of the fenestrations 265 can have non-circular and/or irregular shapes.

In some embodiments, the fenestrations 265 can be marked to facilitate location of the fenestrations 265 during deployment of the stent graft 260 and to facilitate the coupling of branch stents (not shown) with the stent graft 260. For example, the peripheral edges 267A or 267B of the stent graft 260 that define the fenestrations 265A or 265B may be sutured using gold wires and/or wires of other radiopaque materials. Similarly, the location of the fenestration 265 can be marked by one or more radiopaque markers. Such radiopaque wires or markers can facilitate fluoroscopic visualization of the fenestrations 265 during an endovascular repair procedure and allow a physician to locate the fenestration 265 with respect to the corresponding branch vessel. In other embodiments, the fenestrations 265 can be sutured and/or otherwise marked using any suitable material that can increase visibility, for example, when using any suitable imaging device (e.g., MRI scan, CAT scan, PET scan, X-Ray scan, ultrasound, etc.). Such markers can be placed and/or sutured in any suitable manufacturing process, which can be combined with or separate from the formation of the fenestrations 265.

As described above, in some embodiments, a secondary branch stent can be coupled within a fenestration (e.g., fenestrations 265) of a stent graft (e.g., stent graft 260). The relative position of the secondary branch stent can help in the axial and radial alignment and/or positioning of the stent graft 260 with respect to the patients aorta 10 during deployment. During placement of the stent graft the secondary stent can be disposed within a branch vessel (e.g., the SMA 18) extending from a patient's aorta such that the secondary stent can aid in reinforcing the branch vessel in an open position. Additionally, the secondary stent may help maintain the axial and/or radial positioning of the stent graft relative to the patient's aorta (e.g., aorta 10) after placement. The secondary stent may be movable within and/or relative to the fenestration such that a motion of the branch vessel can be accommodated (i.e., vessel tortuosity can be compensated for and vessel kinking can be prevented). In some embodiments, a fenestrated body, such as a main stent graft, can include a flexible portion surrounding a fenestration such that a rigid branch stent engaged with the fenestrated body at the fenestration can rotate within the fenestration. For example, FIG. 5A is a schematic illustration of a front view of a fenestrated body 460. The fenestrated body 460 can be, for example, a main stent graft, such as an aortic stent graft. The fenestrated body 460 can have the same or similar structure and/or function as any of the other fenestrated bodies or stent grafts described herein, such as, for example, stent graft 160 or stent graft 260. The fenestrated body 460 can define a fenestration 465 and include an engagement portion 468 surrounding the fenestration 465. The engagement portion 468 can be flexible and can be configured to engage with a branch stent graft 430 (shown in FIGS. 5B-5D). The branch stent graft 430 can be any suitable stent, such as, for example, a bridge stent or a FEVAR stent.

Figure 5D:
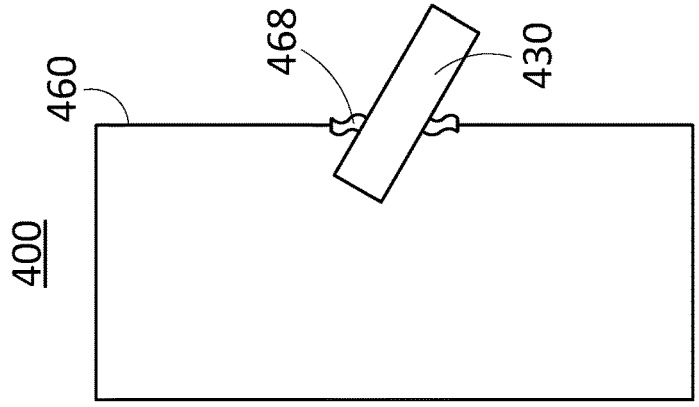
FIGS. 5B-5D are schematic illustrations of a side view of a system in first configuration, a second configuration, and a third configuration, respectively, according to an embodiment.
Figure 5C:
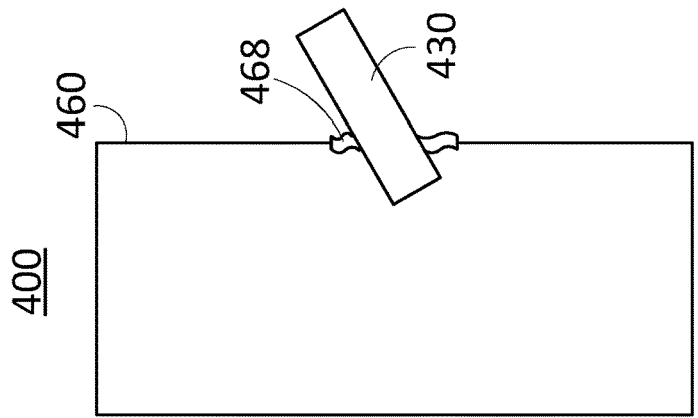
Figure 5B:
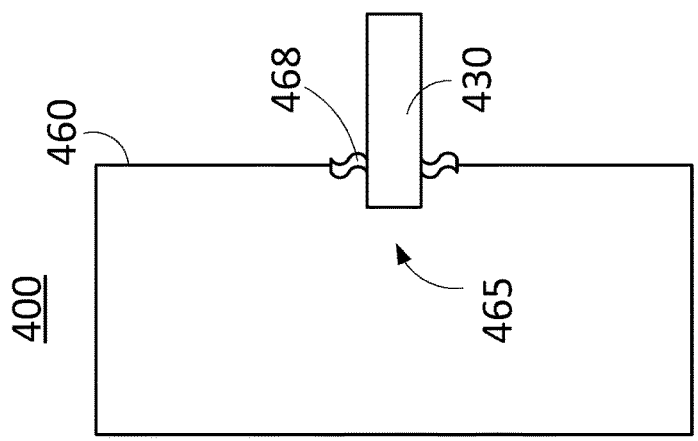
Figure 5A:
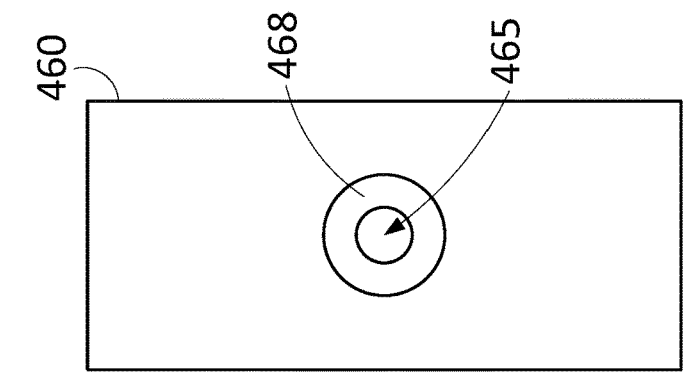
FIG. 5A is a schematic illustration of a front view of a fenestrated body, according to an embodiment.

FIGS. 5B-5D are schematic illustrations of a side view of a system 400 in a first, second, and third configuration, respectively. The system 400 includes the fenestrated body 460 and the branch stent graft 430. The branch stent graft 430 can be rigid or flexible. The engagement portion 468 can be configured such that a plane or face of the engagement portion 468 remains normal to a longitudinal central axis of the branch stent graft 430 as the branch stent graft 430 moves relative to the fenestrated body 460 through the configurations shown in FIGS. 5B-5D. As shown in FIG. 5B, the branch stent graft 430 can be positioned in the first configuration in which the longitudinal central axis of the branch stent graft 430 is perpendicular to a wall of the fenestrated body 460. As shown in FIG. 5C, the branch stent graft 430 can move to a second position (i.e., the second configuration) relative to the branch stent graft 430. As shown in FIG. 5D, the branch stent graft 430 can move to a third position (i.e., the third configuration) relative to the branch stent graft 430. Although the system 400 is shown in FIGS. 5B-5D as having three configurations for illustrative purposes, the system 400 can essentially have an infinite number of configurations. In other words, the engagement portion 468 is sufficiently flexible to allow the longitudinal central axis of the branch stent graft 460 to remain aligned with the branch vessel regardless of movement of the fenestrated body 460.

In some embodiments, the engagement portion 468 can include a flexible locking mechanism (not shown). The flexible locking mechanism can be configured to engage the branch stent graft 430 and maintain the engagement between the flexible locking mechanism and the branch stent graft 430 through a variety of branch stent graft 430 positions. The flexible locking mechanism can also restrict and/or prevent axial movement of the branch stent graft 430 within and/or relative to the fenestration 465 of the fenestrated body 460.

In some embodiments, rather than the fenestrated body including flexible engagement portion, an engagement portion of the fenestrated body can be rigid and an associated branch stent graft can be flexible. For example, FIG. 6 is a schematic illustration of cross-sectional side view of a system 500 that includes a fenestrated body 560 and a flexible branch stent graft 530. The branch stent graft 530 can be any suitable stent, such as, for example, a bridge stent or a FEVAR stent. The fenestrated body 560 can be, for example, a main stent graft, such as an aortic stent graft. The fenestrated body 560 can have the same or similar structure and/or function as any of the other fenestrated bodies or stent grafts described herein, such as, for example, stent graft 160 or stent graft 260. The fenestrated body 560 can define a fenestration 565 and include a rigid engagement portion 568 surrounding the fenestration 565. The engagement portion 568 can be substantially similar to those described in International Patent Application No. PCT/US2017/037157 entitled, "Systems, Devices, and Methods for Marking and/or Reinforcing Fenestrations in Prosthetic Implants" filed Jun. 13, 2017 ("the '157 application"), the disclosure of which is incorporated herein by reference in its entirety.

The flexible branch stent graft 530 can include a proximal end 535 and a distal end 537. The rigid engagement portion 568 can be securely coupled to the proximal end 535 of the flexible branch stent graft 530. The distal end 537 of the flexible branch stent graft 530 can move freely due to the flexibility of the branch stent graft 530. Factors that can influence the flexibility of the branch stent graft 530 can include, for example, the stent pattern, the thickness of the stent material, the type of stent material, and/or the type of connection between the branch stent graft 530 and another stent. The flexible branch stent graft 530 can be moved from a first position to a second position, represented by flexible branch stent graft 530'. In the second position, the proximal end 535 of the flexible branch stent graft 530 remains securely coupled to the rigid engagement portion 568. The distal end 537', however, is disposed in a second position relative to the second end 537 and the flexible branch stent graft 530' is bent into a different shape than when in the first position. Due to the secure attachment between the proximal end 535 of the flexible branch stent graft 530 and the rigid engagement portion 568, the flexible branch stent graft 530 cannot move axially relative to the fenestration 565 and the fenestrated body 560. The secure attachment between the proximal end 535 of the flexible branch stent graft 530 and the rigid engagement portion 568 can be achieved by any suitable coupling structure. For example, the flexible branch stent graft 530 can include a ring with a flange on the proximal end 535.

The flange can be disposed in an abutting arrangement with a portion of the rigid engagement portion 568 facing the interior of the fenestrated body 560. In other implementations, the proximal end 535 of the flexible branch stent graft 530 and the rigid engagement portion 568 can be engaged via a saddle feature, such as the saddle-shaped engagement portion 1031 described below.

In some embodiments, any suitable flexible branch stent graft can be configured to be securely coupled to an engagement portion of a fenestrated body. For example, FIG. 7 is a schematic illustration of cross-sectional side view of system 600 that includes a branch stent graft 630 and a fenestrated body 660. The branch stent graft 630 can be any suitable stent, such as, for example, a bridge stent or a FEVAR stent. The fenestrated body 660 can be, for example, a main stent graft, such as an aortic stent graft. The fenestrated body 660 can have the same or similar structure and/or function as any of the other fenestrated bodies or stent grafts described herein, such as, for example, stent graft 160 or stent graft 260. The fenestrated body 660 can define a fenestration 665 and include an engagement portion 668 surrounding the fenestration 665. The engagement portion 668 can be rigid or flexible and may be configured to be securely coupled to the branch stent graft 630.

The branch stent graft 630 includes a first rigid stent portion 632 and a second rigid stent portion 634. The first rigid stent portion 632 and the second rigid stent portion 634 are coupled by a flexible stent portion 636. Said another way, the flexible branch stent graft 630 can be formed as a unitary stent with a constant, cylindrical outer diameter and can include portions with varying flexibilities or rigidities. Due to the flexibility of the flexible stent portion 636, the branch stent graft 630 can bend and/or rotate relative to the engagement portion 668. For example, the branch stent graft 630 can be bent from a first position in which a central axis of the branch stent graft 630 is perpendicular to a plane or face of the engagement portion 668 to a second position represented by branch stent graft 630' in which the branch stent graft 630' has a curved central axis. As shown, the second rigid stent portion 634' can be shifted to the second position while the first rigid stent portion 632' remains securely coupled to and immobile relative to the engagement portion 668. Additionally, the secure engagement between the first rigid stent portion 632' and the engagement portion 668 can prevent axial movement of the branch stent graft 630 relative to the fenestrated body 660.

In some embodiments, a first flexible stent portion and a second flexible stent portion can be coupled by a rigid stent portion. For example, FIG. 8 is a schematic illustration of cross-sectional side view of system 1200 that includes a branch stent graft 1230 and a fenestrated body 1260. The branch stent graft 1230 can be any suitable stent, such as, for example, a bridge stent or a FEVAR stent. The fenestrated body 1260 can be, for example, a main stent graft, such as an aortic stent graft. The fenestrated body 1260 can have the same or similar structure and/or function as any of the other fenestrated bodies or stent grafts described herein, such as, for example, stent graft 160 or stent graft 260. The fenestrated body 1260 can define a fenestration 1265 and include an engagement portion 1268 surrounding the fenestration 1265. The engagement portion 1268 can be rigid or flexible and may be configured to be securely coupled to the branch stent graft 1230.

The branch stent graft 1230 includes a first flexible stent portion 1232 and a second flexible stent portion 1234. The first flexible stent portion 1232 and the second flexible stent portion 1234 are coupled by a rigid stent portion 1236. Said another way, the branch stent graft 1230 can be formed as a unitary stent with a constant, cylindrical outer diameter and can include portions with varying flexibilities or rigidities. Due to the flexibility of the first flexible stent portion 1232 and the second flexible stent portion 1234, the branch stent graft 1230 can bend and/or rotate relative to the engagement portion 1268. For example, the branch stent graft 1230 can be bent from a first position in which a central axis of the branch stent graft 1230 is perpendicular to a plane or face of the engagement portion 1268 to a second position represented by branch stent graft 1230' in which the branch stent graft 1230' has a varying central axis (i.e., the central axes of the first flexible stent portion 1232 and the second flexible stent portion 1234 are curved). As shown, the first flexible stent portion 1232' and the second flexible stent portion 1234' can be shifted to the second position where each have a second shape, while the rigid stent portion 1236' maintains the same shape in the second position. Additionally, the secure engagement between the first flexible stent portion 1232' and the engagement portion 1268 can prevent axial movement of the branch stent graft 1230 relative to the fenestrated body 1260.

In some embodiments, a branch stent graft can include two rigid portions coupled by a flexible tether. For example, FIG. 9 is a schematic illustration of a cross-sectional side view of a system 700 that includes a flexible branch stent graft 730 and a fenestrated body 760. The branch stent graft 730 can be any suitable stent, such as, for example, a bridge stent or a FEVAR stent. The fenestrated body 760 can be, for example, a main stent graft, such as an aortic stent graft. The fenestrated body 760 can have the same or similar structure and/or function as any of the other fenestrated bodies or stent grafts described herein, such as, for example, stent graft 160 or stent graft 260. The fenestrated body 760 can define a fenestration 765 and include an engagement portion 768 surrounding the fenestration 765. The engagement portion 768 can be rigid or flexible and may be configured to be securely coupled to the branch stent graft 730.

The flexible branch stent graft 730 includes a first rigid stent portion 732 and a second rigid stent portion 734. The first rigid stent portion 732 and the second rigid stent portion 734 are coupled by a flexible bar-like tether 736. The first rigid stent portion 732 and the second rigid stent portion 734 can be the same or different sizes, lengths, and/or shapes. Due to the flexibility of the tether 736, the flexible branch stent graft 730 can bend and/or rotate relative to the engagement portion 768. For example, the flexible branch stent graft 730 can be bent from a first position in which a central axis of the flexible branch stent graft 730 (i.e. a central axis running through the first rigid stent portion 732 and the second rigid stent portion 734) is perpendicular to a plane of the engagement portion 768 to a second position represented by flexible branch stent graft 730' in which the tether 736' is curved. As shown in FIG. 9, the second rigid stent portion 734' can be shifted to the second position while the first rigid stent portion 732' remains securely coupled to and immobile relative to the engagement portion 768. Additionally, the secure engagement between the first rigid stent portion 732 and the engagement portion 768 can prevent axial movement of the branch stent graft 730 relative to the fenestrated body 760.

In some embodiments, a branch stent graft can include a rigid portion and a flexible tail. For example, FIG. 10 is a schematic illustration of cross-sectional side view of a system 800 that includes a branch stent graft 830 and a fenestrated body 860. The branch stent graft 830 can be any suitable stent, such as, for example, a bridge stent or a FEVAR stent. The fenestrated body 860 can be, for example, a main stent graft, such as an aortic stent graft. The fenestrated body 860 can have the same or similar structure and/or function as any of the other fenestrated bodies or stent grafts described herein, such as, for example, stent graft 160 or stent graft 260. The fenestrated body 860 can define a fenestration 865 and include an engagement portion 868 surrounding the fenestration 865. The engagement portion 868 can be rigid or flexible and can be configured to be coupled to the branch stent graft 830.

The flexible branch stent graft 830 includes a rigid stent portion 832, a flexible tail portion 836, and a flexible transition portion 833 coupling the rigid stent portion 832 and the flexible tail portion 836. The flexible transition portion 833 can be less flexible than the flexible tail portion 836 such that the flexible transition portion 833 can provide strain relief between the rigid stent portion 832 and the flexible tail portion 836, thus preventing a kink point or structural fatigue between the rigid stent portion 832 and the flexible tail portion 836. Due to the flexibility of the flexible tail portion 836 and the flexible transition portion 833, the flexible tail portion 836 can bend and/or rotate relative to the rigid stent portion 832 and the engagement portion 868. For example, the flexible tail portion 836 can be bent from a first position in which a central axis of the branch stent graft 830 (i.e. a central axis running through the rigid stent portion 832, the flexible transition portion 833, and the flexible tail portion 836) is perpendicular to a plane of the engagement portion 868 to a second position represented by branch stent graft 830' in which the flexible tail portion 836' is curved. As shown, the flexible tail portion 836' can be shifted to the second position while the first rigid stent portion 832' remains securely coupled to and immobile relative to the engagement portion 868 due to the flexibility of the flexible transition portion 833 and the flexible tail portion 836'. The flexible tail portion 836' can be formed of any suitable material, such as, for example, a metal or metal alloy such as, for example, nickel titanium (nitinol), stainless steel, or cobalt-chromium, and/or a woven polymer or fabric such as, for example, polytetrafluoroethylene (PTFE) or polyethylene terephthalate (PET or Dacron®). Additionally, the secure engagement between the rigid stent portion 832 and the engagement portion 868 can prevent axial movement of the branch stent graft 830 relative to the fenestrated body 860.

In some embodiments, a branch stent graft can be configured to movably engage with an engagement portion of a fenestration body. For example, in some embodiments, both an engagement portion of a fenestrated body and an engagement portion of a branch stent graft can be rigid. The engagement portion of the fenestrated body and the engagement portion of the branch stent graft can engage and/or interlock such that the branch stent graft can move and/or rotate relative to the fenestrated body. For example, FIGS. 11A-11C are schematic illustrations of cross-sectional side views of a system 900 that includes a branch stent graft 930 and a fenestrated body 960. The branch stent graft 930 can be any suitable stent, such as, for example, a bridge stent or a FEVAR stent. The fenestrated body 960 can be, for example, a vessel wall or a main stent graft, such as an aortic stent graft. The fenestrated body 960 can have the same or similar structure and/or function as any of the other fenestrated bodies or stent grafts described herein, such as, for example, stent graft 160 or stent graft 260. The fenestrated body 960 can define a fenestration 965 and include a rigid engagement portion 968 surrounding the fenestration 965. The rigid engagement portion 968 can be configured to be coupled to the branch stent graft 930. In some embodiments, the rigid engagement portion 968 includes a reinforced and/or marked edge of the wall of the fenestrated body 960 in the region surrounding the fenestration 965. In other embodiments, the rigid engagement portion 968 includes the wall of the fenestrated body 960 in the region surrounding the fenestration 965 and is not reinforced.

The branch stent graft 930 can include an engagement portion (not shown) configured to movably couple the branch stent graft 930 to the engagement portion 968 of the fenestrated body 960. Due to the engagement portion of the branch stent graft 930 being movably coupled to the engagement portion 968 of the fenestrated body 960, the branch stent graft 930 can move, pivot, and/or rotate relative to the fenestrated body 960, as shown in FIGS. 11A-11C. Specifically, as shown in FIG. 11A, the branch stent graft 930 can be configured in a first position relative to the fenestrated body 960 such that a central axis of the branch stent graft 930 is perpendicular to a central axis of the fenestrated body 960. The branch stent graft 930 can move relative to the fenestrated body 960 such that the branch stent graft 930 is in a second position relative to the fenestrated body 960, as shown in FIG. 11B. The branch stent graft 930 can move relative to the fenestrated body 960 into a third position relative to the main stent graft 960, as shown in FIG. 11C. Additionally, the engagement between the engagement portion of the branch stent graft 930 and the engagement portion 968 of the fenestrated body 960 can restrict or prevent axial movement of the branch stent graft 930 relative to the fenestrated body 960.

In some embodiments, an engagement portion of a branch stent graft can be formed in any suitable shape. For example, FIG. 12 is a schematic illustration of a cross-sectional side view of a system 1000 that includes a branch stent graft 1030 and a fenestrated body 1060. The branch stent graft 1030 can be any suitable stent, such as, for example, a bridge stent or a FEVAR stent. The fenestrated body 1060 can be, for example, a vessel wall or a main stent graft, such as an aortic stent graft. The fenestrated body 1060 can have the same or similar structure and/or function as any of the other fenestrated bodies or stent grafts described herein, such as, for example, stent graft 160 or stent graft 260. The fenestrated body 1060 can define a fenestration 1065 and include an engagement portion 1068 surrounding the fenestration 1065. The engagement portion 1068 can be configured to be coupled to the branch stent graft 1030. In some embodiments, the engagement portion 1068 includes a reinforced and/or marked edge of the wall of the fenestrated body 1060 in the region surrounding the fenestration 1065. In other embodiments, the engagement portion 1068 includes the wall of the fenestrated body 1060 in the region surrounding the fenestration 1065 and is not reinforced.

The branch stent graft 1030 can include a saddle-shaped engagement portion 1031. The saddle-shaped engagement portion 1031 is configured to be movably coupled to the engagement portion 1068 of the fenestrated body 1060. In some embodiments, the branch stent graft 1030 can be self-expanding. For example, the saddle-shaped engagement portion 1031 can be collapsible and have a biased-expanded shape such that the branch stent graft 1030 can be collapsed for delivery and insertion through the fenestration 1065. Upon being positioned within the fenestration 1065 such that the saddle-shaped engagement portion 1031 is aligned with the engagement portion 1068 of the fenestrated body 1060, the saddle-shaped engagement portion 1031 can be deployed such that the saddle-shaped engagement portion 1031 automatically assumes an expanded configuration and engages with the engagement portion 1068 of the fenestrated body 1060, as shown in FIG. 12.

In other embodiments, the engagement portion 1031 or the entire branch stent graft 1030 can be moldable and radially expandable. A separate expandable member, such as a balloon, can be used to expand and/or shape the branch stent graft 1030 after the branch stent graft 1030 has been delivered to the target location relative to the engagement portion 1068 of the fenestrated body 1060. The expandable member can be expanded such that the engagement portion 1031 of the branch stent graft 1030 is shaped via the force the expandable member applies to the inner surface of the engagement portion 1031. In some embodiments, the expandable member can be pre-shaped such that the unconstrained, expanded shape of the expandable member includes two larger diameter portions separated by a smaller diameter portion (e.g., an hourglass shape). The pre-shaped expandable member can apply pressure to the inner surface of the engagement portion 1031 such that the engagement portion 1031 takes a similar shape. In other embodiments, the expandable member can have an unconstrained, cylindrical expanded shape, and the expandable member can be limited in expansion by the engagement portion 1068 of the fenestrated body 1060 such that the expandable member can only expand on either side of the engagement portion 1068. As a result, the expandable member can only apply expansion force to the inner surface of the engagement portion 1031 on either side of the engagement portion 1068, causing the engagement portion 1031 of the branch stent graft 1030 to be shaped as shown in FIG. 12. The expandable member can be compliant or non-compliant.

In some embodiments, the system 1000 can include a stop feature such that the user can determine when the engagement portion 1031 of the branch stent graft 1030 and the engagement portion 1068 of the fenestrated body 1060 are appropriately aligned for deployment and/or expansion of the engagement portion 1031. The stop feature can be located on a delivery device used to deliver the branch stent graft 1030, on the engagement portion 1068, and/or on the engagement portion 1031. In some embodiments, the stop feature can be located on an expandable member, such as a balloon, that is used to expand and/or shape the branch stent graft 1030. For example, when the expandable member is in a first expanded configuration, the stop feature can engage an anatomical feature, such as the aorta wall, such that a user is alerted that the expandable member is properly located. The expandable member can then be moved to a second expanded configuration to apply pressure to the inner surface of the engagement portion 1031 such that the engagement portion 1031 is forced into the desired shape. In some embodiments, radiopaque markers, such as, for example, bands, can be disposed on the branch stent graft 1030 and/or the engagement portion 1068 such that the relative positions of the branch stent graft 1030 and the engagement portion 1068 can be visually confirmed before deployment and/or expansion of the engagement portion 1031.

When the saddle-shaped engagement portion 1031 is engaged with the engagement portion 1068 of the fenestrated body 1060, the branch stent graft 1030 can move pivotally or rotationally relative to the engagement portion 1068 of the fenestrated body 1060. The saddle-shaped engagement portion 1031 can include a flared distal end to restrict or prevent axial movement of the branch stent graft 1030 relative to the fenestrated body 1060 while still allowing movement (e.g., pivotal, rotational, etc.) relative to the fenestrated body 1060.

Figure 13B:
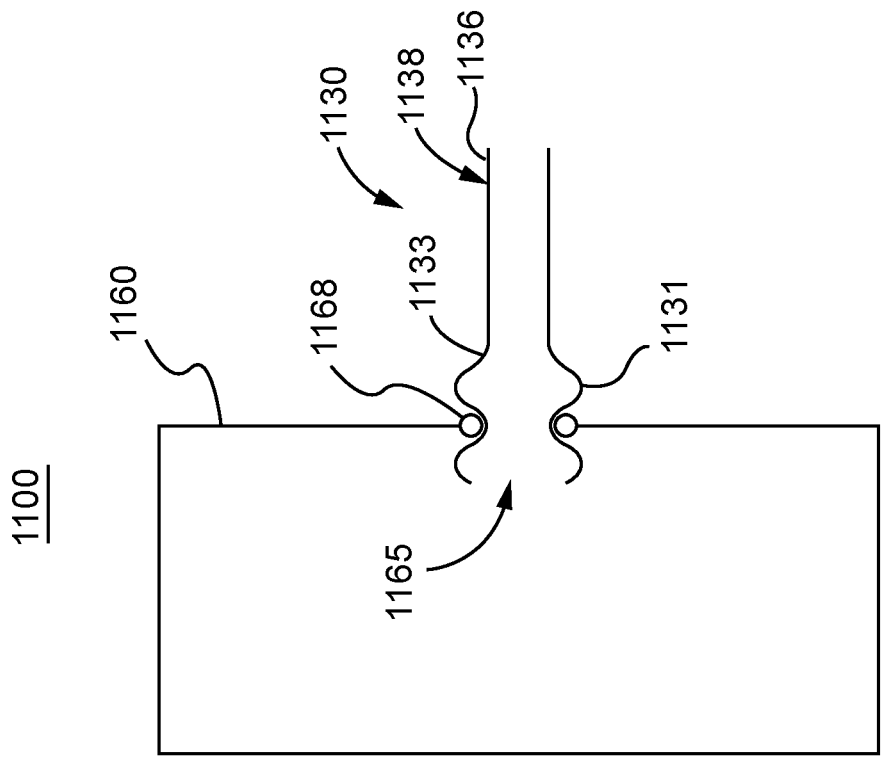
FIG. 13B is a schematic illustration of a cross-sectional side view of the system of FIG. 13A in a second configuration.
Figure 13A:
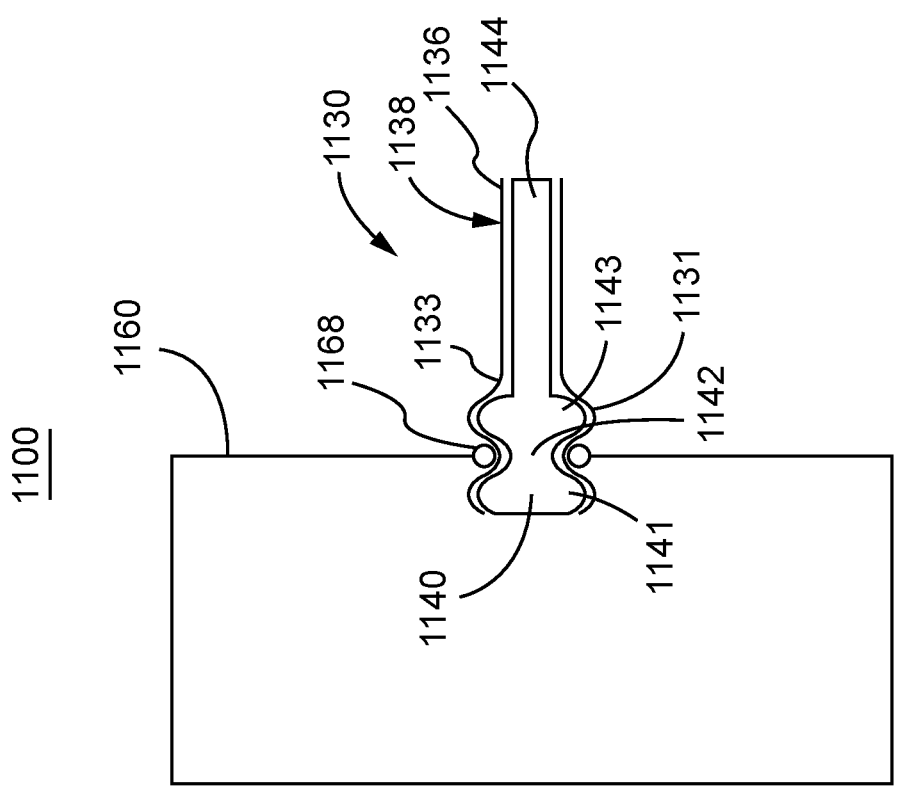
FIG. 13A is a schematic illustration of a cross-sectional side view of a system, according to an embodiment, in a first configuration.

In some embodiments, the saddle-shaped engagement portion of a branch stent graft can have any suitable shape. For example, FIG. 13A is a schematic illustration of a cross-sectional side view of a system 1100 that includes a branch stent graft 1130 and a fenestrated body 1160. The branch stent graft 1130 can be any suitable stent, such as, for example, a bridge stent or a FEVAR stent. The fenestrated body 1160 can be, for example, a vessel wall or a main stent graft, such as an aortic stent graft. The fenestrated body 1160 can have the same or similar structure and/or function as any of the other fenestrated bodies or stent grafts described herein, such as, for example, stent graft 160 or stent graft 260. The fenestrated body 1160 can define a fenestration 1165 and include an engagement portion 1168 surrounding the fenestration 1165. The engagement portion 1168 can be configured to be coupled to the branch stent graft 1130. In some embodiments, the engagement portion 1168 includes a reinforced and/or marked edge of the wall of the fenestrated body 1160 in the region surrounding the fenestration 1165. In other embodiments, the engagement portion 1168 includes the wall of the fenestrated body 1160 in the region surrounding the fenestration 1165 and is not reinforced.

The branch stent graft 1130 can include a saddle-shaped or an hour-glass shaped engagement portion 1131. The saddle-shaped engagement portion 1031 is configured to be rotatably coupled to the engagement portion 1168 of the fenestrated body 1160. In such a configuration, the branch stent graft 1130 can move relative to the engagement portion 1168 of the fenestrated body 1160.

In some embodiments, the engagement portion 1131 can be moldable and an expandable member can be used to shape the engagement portion 1131. As shown in FIG. 13A, the system 1100 can include an expandable member 1140. The expandable member 1140 can be fluidically coupled to a fluid supply mechanism (not shown) that can be controlled during deployment. After the engagement portion 1131 is positioned within the fenestration 1165, the expandable member 1140 can be inserted into the fenestration 1165 and aligned with the engagement portion 1131 of the branch stent graft 1130 and the engagement portion 1168 of the fenestrated body 1160. The expandable member 1140 can then be expanded by, for example, using the fluid supply mechanism coupled to the expandable member, such that the engagement portion 1131 of the branch stent graft 1130 is shaped via the force the expandable member 1140 applies to the inner surface of the engagement portion 1131.

In some embodiments, the expandable member 1140 can be pre-shaped such that the unconstrained, expanded shape of the expandable member 1140 includes a first portion proximal to the fenestrated body 1160 and a second portion 1144 distal to the fenestrated body 1160. The proximal portion further includes a first large diameter portion 1141, a second smaller diameter portion 1142 distal to the first large diameter portion 1141, and a third larger diameter portion 1143 distal to the second smaller diameter portion 1142, as shown in FIG. 13A. The first, second, and third diameter portions of the first proximal portion form a saddle-shape or an hourglass shape of the expandable member 1140. The first diameter of portion 1141 may be comparable or slightly larger or slightly smaller than the diameter of the third diameter of portion 1143. The second small diameter portion 1142 forms the valley portion that engages with the engagement portion 1168 of the fenestrated body 1160.

The distal portion 1144 of the expandable member 1140 can be configured to have a smaller diameter than the proximal portion containing the saddle-shape. Further, the distal portion 1140 can be configured to engage with the tail portion 1136 of the branch stent graft 1130 upon expansion, by applying expansion force to the inner side of the branch stent graft. Thus the distal portion 1144 of the pre-shaped expandable member 1140 can cause the tail portion 1136 of the branch stent graft 1130 to adopt a desired shape. Similarly, the proximal portion of the expandable member 1140 can apply expansion force to the inner side of the proximal regions of the branch stent graft 1130 to cause the branch stent graft to assume a desired shape.

The proximal portion of the expandable member 1140 (including the first 1141, second 1142, and third diameter 1143 portions) and the distal portion 1144 of the expandable member 1140 can be fluidically coupled to a single fluid supply mechanism or be separately connected to distinct fluid supply mechanisms to control their expansion during deployment. The pre-shaped expandable member 1140 can be used to apply pressure to the inner surface of the engagement portion 1131 such that the engagement portion 1131 takes a similar shape.

In some embodiments, the expandable member 1140 can be semi-compliant. In some embodiments, the proximal portion of the expandable member 1140 including the first 1141, second, 1142, and the third 1143 diameter portions forming the saddle-shape can be semi-compliant and the distal portion of the expandable member 1140 can be non-compliant. In some embodiments, the proximal and the distal portions can both be compliant, with the proximal portion having greater compliance than the distal portion of the expandable member 1140. In some embodiments, the distal portion can have a substantially comparable compliance or greater compliance than the proximal portion of the expandable member 1140.

As described above, rather than including a flared proximal end when fully expanded like the saddle-shaped engagement portion 1031 shown in FIG. 12, the saddle-shaped engagement portion 1131, upon expansion, can include two larger diameter portions connected by a smaller diameter valley portion. The engagement portion 1168 of the fenestrated body 1160 can engage with the valley portion such that the two larger diameter portions prevent the branch stent graft 1130 from being moved axially away from the main stent graft 1160 while still allowing rotational movement relative to the main stent graft 1160.

In some embodiments, the saddle-shaped engagement portion 1131 when expanded may be shaped such that the third diameter portion has a larger diameter than the first diameter portion, while both the first and the third portion have a larger diameter than the second portion that forms the valley portion for engagement with the fenestrated body 1160. In some other embodiments, the third diameter portion may have a smaller diameter than the first portion and a larger diameter than the second valley portion that still is configured to engage with the fenestrated body 1160 and prevent axial movement of the branch stent graft 1130, upon expansion In some other embodiments, the first and third portions of the saddle-shaped engagement portion 1131, when fully expanded, may have substantially equal diameter while the second portion has a smaller diameter and engages with the fenestrated body 1160 to prevent axial movement of the branch stent graft 1130 while allowing pivotal or rotational movement of the branch stent graft about the fenestrated body 1160.

In some embodiments, the saddle-shaped engagement portion of the branch stent graft 1130 and the engagement portion 1168 of the fenestrated body 1160 can be configured such that upon deployment the distal portion of the branch stent 1130 (including, for example, the third diameter portion of the saddle-shaped engagement portion 1131) is disposed outside the fenestrated body 1160 and the proximal portion of branch stent (including, for example, the first diameter portion of the saddle-shaped engagement portion 1131) is disposed inside the fenestrated body 1160. Further, the intermediate portion (for example, the second diameter portion of the saddle-shaped engagement portion 1131 forming the valley portion) can be configured to be frictionally engage or engage through an interference fit with the opening or fenestration in the engagement portion of the fenestrated body 1160.

In some embodiments, rather than using an expandable member, the saddle-shaped engagement portion 1131 can be collapsible and have a biased-expanded shape such that the branch stent graft 1130 can be collapsed for delivery and insertion through the fenestration 1165. Upon being positioned within the fenestration 1165 such that the saddle-shaped engagement portion 1131 is aligned with the engagement portion 1168 of the fenestrated body 1160, the saddle-shaped engagement portion 1131 can be deployed such that the saddle-shaped engagement portion 1131 assumes an expanded configuration (e.g., the configuration shown in FIG. 13B) and engages with the engagement portion 1168 of the fenestrated body 1160.

In some embodiments, the system 1100 can include a stop feature such that the user can determine when the engagement portion 1131 of the branch stent graft 1130 and the engagement portion 1168 of the fenestrated body 1160 are appropriately aligned for deployment and/or expansion of the engagement portion 1131. The stop feature can be located on a delivery device used to deliver the branch stent graft 1130, on the engagement portion 1168, and/or on the engagement portion 1131. In some embodiments, the stop feature can be located on the expandable member 1140. For example, when the expandable member 1140 is in a first expanded configuration, the stop feature can engage an anatomical feature, such as the aorta wall, such that a user is alerted that the expandable member 1140 is properly located. The expandable member 1140 can then be moved to a second expanded configuration to apply pressure to the inner surface of the engagement portion 1131 such that the engagement portion 1131 is forced into the desired shape. In some embodiments, radiopaque markers, such as, for example, bands, can be disposed on the branch stent graft 1130 and/or the engagement portion 1168 such that the relative positions of the branch stent graft 1130 and the engagement portion 1168 can be visually confirmed before deployment and/or expansion of the engagement portion 1131.

As described above, the system 1300 in FIG. 14 can be substantially similar to other systems described herein. For example, the system 1300 can be similar to the system 500 illustrated in FIG. 6, or to the system 600 illustrated in FIG. 7, or the system 800 illustrated in FIG. 10. As an example, the branch stent graft 1130 can be substantially similar to the branch stent 630 and the fenestrated body 1160 can be substantially similar to the fenestrated body 660. Additionally, the engagement portion 1131 of the branch stent 1130 can be suitably rigid or flexible to engage with the fenestrated body 1160 at the engagement portion 1168. The engagement portion 1131 of branch stent 1130 can include a transition portion 1133 and a distal tail portion 1136 defining a longitudinal central axis. Additionally, the branch stent 1130 can be suitably flexible or rigid to couple with the fenestrated body 1160 and maintain the longitudinal central axis substantially perpendicular to the plane defined by the opening in the fenestrated body 1160.

In some embodiments, the branch stent 1130 can include a tail portion 1136 that is configured to have a flexibility greater than the flexibility of the engagement portion. For example, the flexibility of the tail portion can be 25% greater than the flexibility of the engagement portion 1131 of the branch stent graft 1130. In some other embodiments, the flexibility of the tail portion may be comparable to or lesser than the flexibility of the engagement portion 1131.

In some embodiments, the tail portion 1136 of the branch stent graft 1130 can include a cover 1138 made of a suitable material of suitable thickness and having a strain capability to impart the desired flexibility to the branch stent 1130 and allow the branch stent graft to expand. For example, the cover 1138 may be formed of one or more layers of a suitable material with a suitable microstructure such that the flexibility of the branch stent graft 1130 can be precisely controlled. As an example, the cover 1138 can be configured to have a strain capability to support expansion of the branch stent from a first diametrical size (e.g. about 2 mm) to a second substantially expanded diametrical size (e.g. about 4-12 mm) with no failure. That is, the strain capability of the cover 1138 can be designed to withstand a branch stent expansion in the example ranges of 2 mm-4 mm to 2 mm-12 mm. In some embodiments, the cover can have strain capability of at least about two times, at least about three times, at least about four times, or at least about five times the diametrical expansion of the engagement portion without experiencing a failure (e.g., a rip, a tear, etc.).

In some embodiments, the cover 1138 described above can be disposed over the flexible tail portion 1136, the engagement portion 1131, the transition portion, or any combination thereof. In other words, the cover can be disposed over any individual portion of the branch stent graft 1130, multiple portions, or the entire branch stent graft 1130. Further, the cover 1138 disposed over the engagement portion 1131, transition portion 1133, and/or the tail portion 1136 of the branch stent graft 1130 can be configured to impart the desired flexibility to each of the engagement, transition, and tail portions of the branch stent 1130. For example, the cover disposed over one or more of the portions described above can be of a suitable material with a suitable microstructure, and can be made suitably thick with a suitable number of layers to render the desired flexibility with substantially precise control.

The transition portion of the branch stent 1130 can be suitably flexible or rigid to prevent any kink formation or structural fatigue between the fenestrated body 1160 and the branch stent 1130. For example, in some embodiments, the flexibility of the transition portion 1133 of the branch stent 1130 can be greater than the flexibility of the engagement portion 1131 and less than the flexibility of the flexible tail portion of the branch stent 1130. In other words, the tail portion 1136 can be configured to be substantially more flexible than the transition portion 1133 as well as the engagement portion 1131. For example, the flexibility of the tail portion 1136 of the branch stent 1130 can be configured such that the branch stent 1130 deflects from its longitudinal axis by at least about 1 mm, at least about 2 mm, at least about 3 mm, or at least about 4 mm at a longitudinal distance of 20 mm away from the engagement portion 1131 of the branch stent, when a deflecting force of less than 1 N is used. Said another way, the flexible tail portion defines a longitudinal central axis in a first, unstressed state, and is configured to deflect to a second, stressed state when a deflecting force of less than about 1 N is applied at a longitudinal distance 20 mm away from the engagement portion. When such a deflection force is applied, the flexible tail portion moves at least about 1 mm, at least about 2 mm, at least about 3 mm, or at least about 4 mm from the first state to the second state. In some other embodiments, the transition portion 1133 can be configured to have a flexibility comparable to or lesser than the engagement portion 1131 and/or the tail portion of the branch stent 1130.

Figure 14:
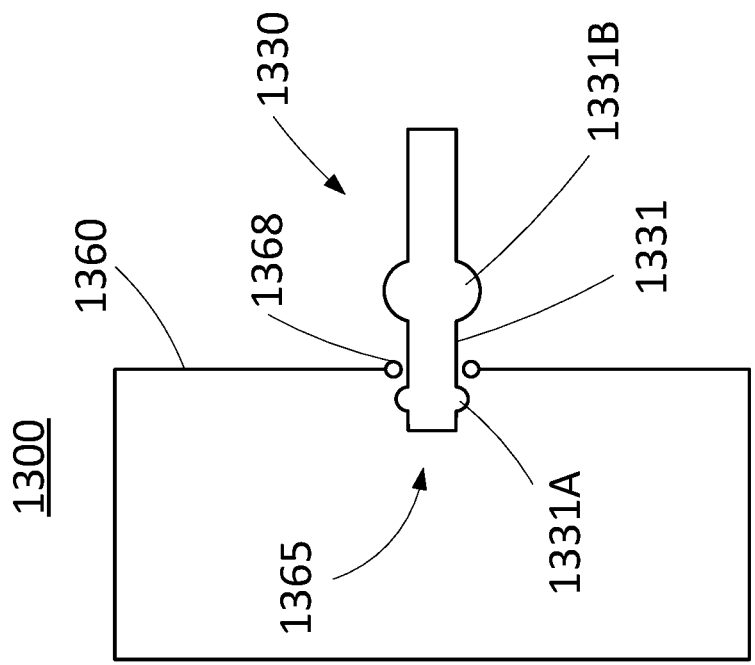
FIG. 14 is a schematic illustration of a cross-sectional side view of a system, according to an embodiment.

FIG. 14 is a schematic illustration of a cross-sectional side view of a system 1300 including another shape of a branch stent graft 1330, according to an embodiment. As shown in FIG. 14, the system 1300 includes the branch stent graft 1330 and a fenestrated body 1360. The branch stent graft 1330 can be any suitable stent, such as, for example, a bridge stent or a FEVAR stent. The fenestrated body 1360 can be, for example, a vessel wall or a main stent graft, such as an aortic stent graft. The fenestrated body 1360 can have the same or similar structure and/or function as any of the other fenestrated bodies or stent grafts described herein, such as, for example, stent graft 160 or stent graft 260. The fenestrated body 1360 can define a fenestration 1365 and include an engagement portion 1368 surrounding the fenestration 1365. The engagement portion 1368 can be configured to be coupled to the branch stent graft 1330. In some embodiments, the engagement portion 1368 includes a reinforced and/or marked edge of the wall of the fenestrated body 1360 in the region surrounding the fenestration 1365. In other embodiments, the engagement portion 1368 includes the wall of the fenestrated body 1360 in the region surrounding the fenestration 1365 and is not reinforced.

The branch stent graft 1330 can include an engagement portion 1331. The engagement portion 1331 can include a first larger diameter position 1331A and a second larger diameter portion 1331B. The engagement portion 1331 can be coupled to the engagement portion 1368 of the fenestrated body 1360 such that the engagement portion 1368 of the fenestrated body 1360 is positioned between the first larger diameter portion 1331A and the second larger diameter portion 1331B. Thus, the branch stent graft 1330 can move relative to the engagement portion 1368 of the fenestrated body 1360. The first larger diameter portion 1331A and the second larger diameter portion 1331B can each be a larger diameter than the diameter of the fenestration 1365 defined by the engagement portion 1368 of the fenestrated body 1360, thus restricting or preventing axial movement of the branch stent graft 1330 with respect to the main stent graft 1360 while still allowing rotational and/or pivotal movement relative to the main stent graft 1360. Although the first larger diameter portion 1331A is shown as being smaller in size than the second larger diameter portion 1331B, in some embodiments the first larger diameter portion 1331A can be the same size as or a larger size that the second larger diameter portion 1331B.

Figure 15:
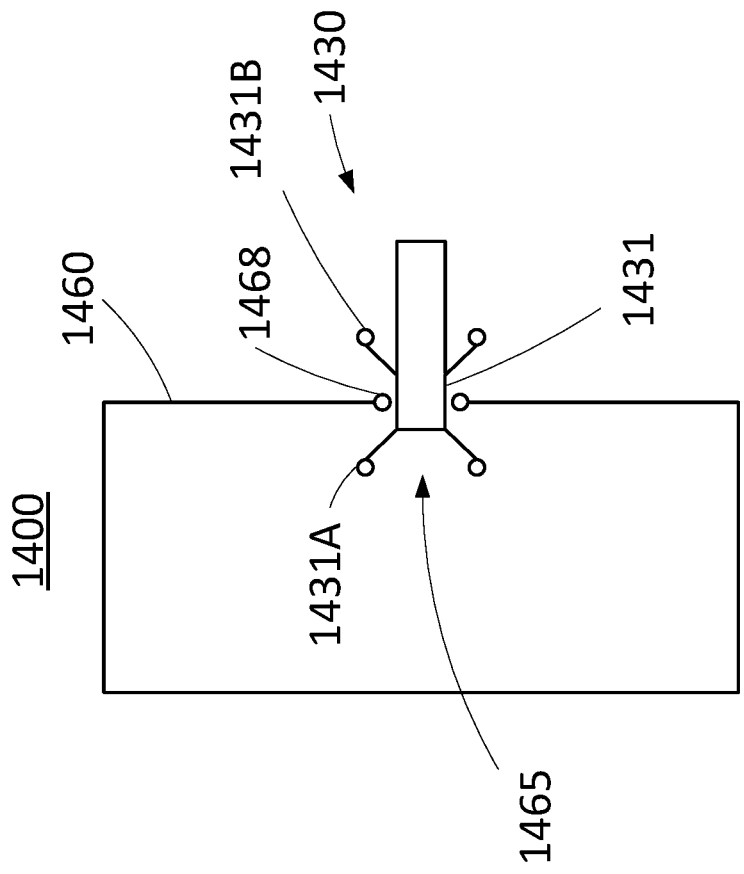
FIG. 15 is a schematic illustration of a cross-sectional side view of a system, according to an embodiment.

FIG. 15 is a schematic illustration of a cross-sectional side view of a system 1400. The system 1400 includes a branch stent graft 1430 having a double-sided engagement portion 1431. The system 1400 also includes a fenestrated body 1460. The branch stent graft 1430 can be any suitable stent, such as, for example, a bridge stent or a FEVAR stent. The fenestrated body 1460 can be, for example, a vessel wall or a main stent graft, such as an aortic stent graft. The fenestrated body 1460 can have the same or similar structure and/or function as any of the other fenestrated bodies or stent grafts described herein, such as, for example, stent graft 160 or stent graft 260. The fenestrated body 1460 can define a fenestration 1465 and include an engagement portion 1468 surrounding the fenestration 1465. The engagement portion 1468 can be configured to be coupled to the branch stent graft 1430. In some embodiments, the engagement portion 1468 includes a reinforced and/or marked edge of the wall of the fenestrated body 1460 in the region surrounding the fenestration 1465. In other embodiments, the engagement portion 1468 includes the wall of the fenestrated body 1460 in the region surrounding the fenestration 1465 and is not reinforced.

The double-sided engagement portion 1431 is configured to be movably coupled to the engagement portion 1468 of the fenestrated body 1460. The engagement portion 1431 of the branch stent graft 1430 includes a first engagement feature 1431A and a second engagement feature 1431B. The engagement portion 1431 (and thus, the first engagement feature 1431A and the second engagement feature 1431B) can be any suitable shape capable of engaging the engagement portion 1468 from the inside and/or the outside of the fenestrated body 1460. For example, in some implementations, the first engagement feature 1431A and the second engagement feature 1431B can be structured and attached to the fenestrated body 1460 in a similar manner to a patent foramen ovale (PFO) closure device with a stent attached.

In some implementations, the first engagement feature 1431A and the second engagement feature 1431B can each be formed as expandable rings and disposed on either side of the engagement portion 1468. The first engagement feature 1431A can be positioned on a first side of the engagement portion 1468 (e.g., inside the fenestrated body 1460). The second engagement feature 1431B can be positioned on a second side of the engagement portion 1468 opposite the first side (e.g. outside the fenestrated body 1460). The engagement portion 1431 can be coupled to the engagement portion 1468 of the main stent graft 1460 such that the engagement portion 1468 of the fenestrated body 1460 is movably secured between the first engagement feature 1431A on the first side and the second engagement feature 1431B on the second side. In such a configuration, the branch stent graft 1430 can rotate and/or shift relative to the engagement portion 1468 of the fenestrated body 1460. The diameter of the first engagement feature 1431A and the second engagement feature 1431B can be larger than the diameter of the fenestration defined by the engagement portion 1468, thus preventing the branch stent graft 1430 from moving axially away from the fenestrated body 1460 while still allowing rotational movement relative to the fenestrated body 1460.

In some implementations, the engagement portion 1431 of the branch stent graft 1430 includes an X-shaped saddle such that the first engagement feature 1431A includes a first prong element and a second prong element and the second engagement feature 1431B includes a third prong element and a fourth prong element. The first prong element and the second prong element can be positioned on a first side of the engagement portion 1468 (e.g., inside the fenestrated body 1460). The third prong element and the fourth prong element can be positioned on a second side of the engagement portion 1468 opposite the first side (e.g. outside the fenestrated body 1460). The engagement portion 1431 can be coupled to the engagement portion 1468 of the main stent graft 1460 such that the engagement portion 1468 of the fenestrated body 1460 is movably secured between the first prong element and the third prong element on the first side and between the second prong element and the fourth prong element on the second side. In such a configuration, the branch stent graft 1430 can rotate and/or shift relative to the engagement portion 1468 of the fenestrated body 1460. A distance between the first prong element and the second prong element and a distance between the third prong element and the fourth prong element can be larger than the diameter of the fenestration defined by the engagement portion 1468, thus preventing the branch stent graft 1430 from moving axially away from the fenestrated body 1460 while still allowing rotational movement relative to the fenestrated body 1460.

In some embodiments, a branch stent graft can include an anchoring member for engagement with an internal wall of a fenestrated body, such as a main stent graft or a vessel wall. For example, FIGS. 16A-16E are schematic illustrations of various views and configurations of a system 1500. The system 1500 includes a branch stent graft 1530 including an anchoring member 1550 and a fenestrated body 1560. The branch stent graft 1530 can be any suitable stent, such as, for example, a bridge stent or a FEVAR stent. The fenestrated body 1560 can be, for example, a vessel wall or a main stent graft, such as an aortic stent graft. The fenestrated body 1560 can have the same or similar structure and/or function as any of the other fenestrated bodies or stent grafts described herein, such as, for example, stent graft 160 or stent graft 260. The fenestrated body 1560 can define a fenestration 1565 and include an engagement portion 1568 surrounding the fenestration 1565. The engagement portion 1568 can be configured to be coupled to the branch stent graft 1530. In some embodiments, the engagement portion 1568 includes a reinforced and/or marked edge of the wall of the fenestrated body 1560 in the region surrounding the fenestration 1565. In other embodiments, the engagement portion 1568 includes the wall of the fenestrated body 1560 in the region surrounding the fenestration 1565 and is not reinforced.

Figure 16A:
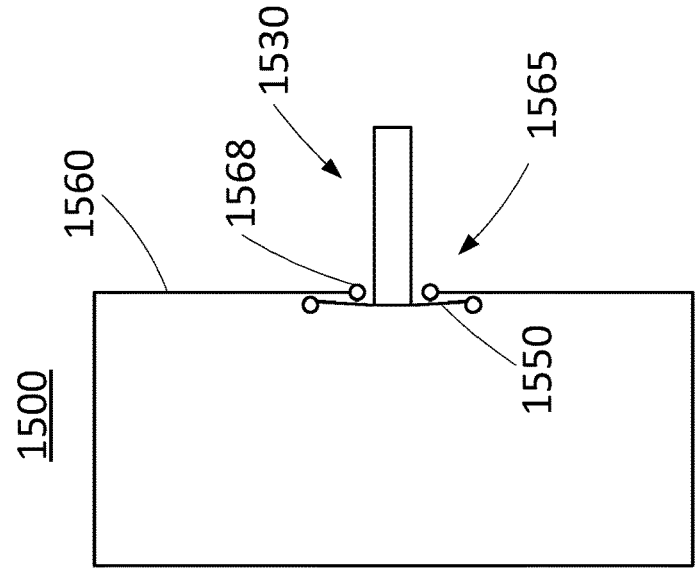
FIG. 16A is a schematic illustration of a cross-sectional side view of a system, according to an embodiment, in a first configuration.
Figure 16B:
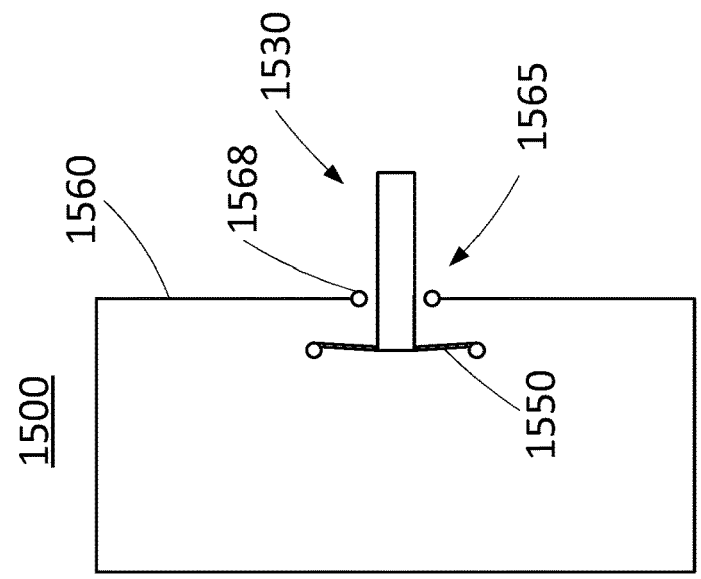
FIG. 16B is a schematic illustration of a cross-sectional side view of the system of FIG. 16A in a second configuration.
Figure 16C:
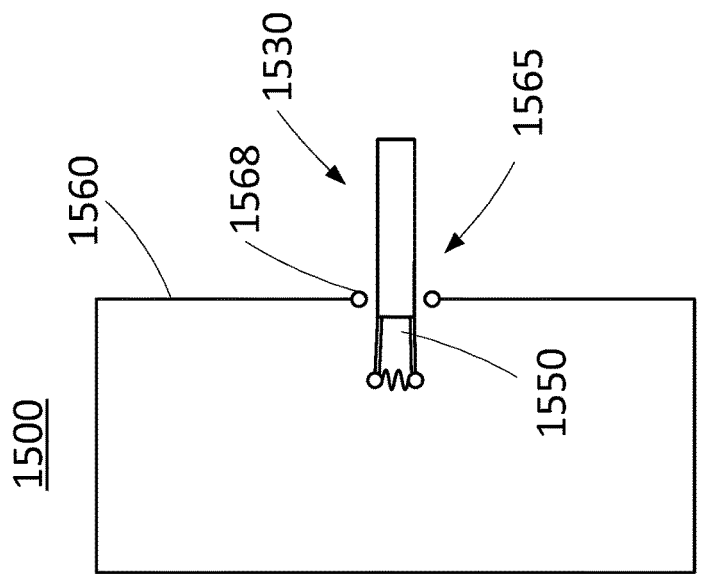
FIG. 16C is a schematic illustration of a cross-sectional side view of the system of FIG. 16A in a third configuration.

The anchoring member 1550 can be in the form of a parachute or a flared end portion of the branch stent graft 1530. The anchoring member 1550 can be movable from a collapsed, delivery configuration to an expanded, anchoring configuration. As shown in FIG. 16A, which is a schematic illustration of a cross-sectional side view of the system 1500 in a first configuration, the anchoring member 1550 can be delivered to the fenestration 1565 in the collapsed, delivery configuration. In some embodiments, the anchoring member 1550 can be delivered to the fenestration within a delivery tube (not shown). The anchoring member 1550 can be biased toward the expanded configuration such that the anchoring member 1550 can be compressed within the delivery tube and then automatically moved to the expanded configuration upon being removed from the delivery tube. As shown in FIG. 16B, which is a schematic illustration of a cross-sectional side view of the system 1500 in a second configuration, the anchoring member 1550 can expand to the expanded, anchoring configuration after, for example, being delivered from an end of the delivery tube. Once the anchoring member 1550 is deployed to the expanded, anchoring configuration, the anchoring member 1550 can be positioned against the internal surface of the wall of the fenestrated body 1560 such that the anchoring member 1550 is engaged with the engagement portion 1568 of the fenestrated body 1560 (e.g. such that the anchoring member 1550 abuts the engagement portion 1568) as shown in FIG. 16C. In such a configuration, the branch stent graft 1530 can be positioned such that the branch stent graft 1530 extends through the fenestration 1565 but cannot move axially relative to the fenestration 1530. As shown in FIG. 16D, once the anchoring member 1550 is positioned in an engaged relationship with the engagement portion 1568, the branch stent graft 1530 can be expanded, such as via an expandable member (e.g., a balloon), within the fenestration 1565. FIG. 16E is a schematic illustration of the internal wall of the fenestrated body 1560 with the anchoring member 1550 secured to the engagement portion 1568 of the fenestrated body 1560. In some embodiments, the anchoring member 1550 and the branch stent graft 1530 can be attached to the fenestrated body in a similar manner to a patent foramen ovale (PFO) closure device with a stent attached.

Although only one anchoring member 1550 is shown in FIGS. 16A-16E, in some embodiments, a second anchoring member could be included such that the second anchoring member engages the outside wall of the fenestrated body 1560. For example, a self-expanding parachute can be disposed on the branch stent graft 1530 such that a first self-expanding parachute can open on the inside of the fenestrated body 1560 and a second self-expanding parachute can open on the outside of the fenestrated body 1560, securing the branch stent graft 1530 to the fenestrated body 1560.

In use, as described above, the branch stent graft 1530 can be delivered to a target location using a deployment device. For example, the branch stent graft 1530 can be delivered over a guidewire through the fenestrated body 1560, and out the fenestration 1565 of the fenestrated body 1560 into a branch artery (not shown in FIGS. 16A-16E). In some implementations, a delivery tube can be used to position the branch stent graft 1530 such that the anchoring member 1550 is within a lumen of the fenestrated body 1560 and another portion of the branch stent graft 1530 is within a branch artery (similar to the configuration shown in FIG. 16A). In this position, the anchoring member 1550 (e.g., a parachute) can be deployed (similar to the configuration shown in FIG. 16B). For example, the anchoring member 1550 or the entire branch stent graft 1530 can be pushed out of an end of the delivery tube and automatically expand to the configuration shown in FIG. 16B. The anchoring member 1550 can then be pushed toward the fenestration 1530 such that the anchoring member 1550 abuts the area of the fenestrated body surrounding the fenestration (e.g., the engagement portion 1568, as shown in FIG. 16C). With the anchoring member abutting the wall and/or the engagement portion of the fenestrated body, the branch stent graft 1530 can be axially expanded within the fenestration 1565 and the branch artery (as shown in the configuration shown in FIG. 16D). For example, an expandable member (e.g., a balloon) can be inserted into a lumen of the branch stent graft 1530 and expanded, thus causing the branch stent graft 1530 to expand to a wider-diameter configuration within the fenestration 1565.

While various embodiments of the system, methods and devices have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and such modifications are in accordance with the variations of the invention. Additionally, certain of the steps may be performed concurrently in a parallel process when possible, as well as performed sequentially as described above. The embodiments have been particularly shown and described, but it will be understood that various changes in form and details may be made.

For example, although various embodiments have been described as having particular features and/or combinations of components, other embodiments are possible having any combination or sub-combination of any features and/or components from any of the embodiments described herein in addition, the specific configurations of the various components can also be varied. For example, the size and specific shape of the various components can be different than the embodiments shown, while still providing the functions as described herein.

The invention claimed is:

1. A radially expandable branch stent graft assembly, comprising:
   an engagement portion for engaging with an opening in fenestrated body, the engagement portion configured to allow the branch stent graft to pivot about the opening of the fenestrated body and to limit axial movement of the branch stent graft relative to the fenestrated body;
   a flexible tail portion extending from the engagement portion; and
   a transition portion disposed between the engagement portion and the flexible tail portion, the transition portion having a flexibility greater than the engagement portion and less than the flexible tail portion.

2. The branch stent graft assembly of claim 1, wherein the engagement portion includes a proximal portion having a first diameter, an intermediate portion having a second diameter, and a distal portion having a third diameter, the second diameter less than the first diameter and the third diameter in an expanded state.

3. The branch stent graft assembly of claim 2, wherein the proximal portion is configured to be disposed on an inside of the fenestrated body, the distal portion is configured to be disposed on an outside of the fenestrated body, and the intermediate portion is configured to frictionally engage with the opening of the fenestrated body.

4. The branch stent graft assembly of claim 1, wherein the engagement portion is rigid.

5. The branch stent graft assembly of claim 1, wherein the engagement portion is flexible.

6. The branch stent graft assembly of claim 1, wherein the engagement portion and the transition portion define a longitudinal central axis, the engagement portion configured to maintain the longitudinal central axis substantially perpendicular to a plane defined by the opening in the fenestrated body.

7. The branch stent graft assembly of claim 1, wherein the flexibility of the flexible tail portion is imparted by at least one of a stent pattern, a stent thickness, and a stent material.

8. The branch stent graft assembly of claim 1, wherein at least a portion of the flexible tail has a cover.

9. The branch stent graft assembly of claim 8, wherein flexibility of the flexible tail portion is controlled by at least one of a cover thickness, a cover material, a cover microstructure, and a number of layers of covering.

10. The branch stent graft assembly of claim 8, wherein the cover has a strain capability of at least about five times diametrical expansion of the engagement portion.

11. The branch stent graft assembly of claim 1, wherein the flexible tail portion has a flexibility at least about 25% greater than the engagement portion.

12. The branch stent graft assembly of claim 1, wherein the flexible tail portion defines a longitudinal central axis in a first state, the flexible tail portion configured to deflect from the first state to a second state when a deflecting force of less than about 1 N is applied.

13. The branch stent graft assembly of claim 12, wherein the flexible tail portion is configured to move at least about 3 mm at a longitudinal distance of 20 mm away from the engagement portion.

14. A radially expandable branch stent graft assembly, comprising:
   a saddle-shaped engagement portion for engaging with an opening in a fenestrated body, the saddle-shaped engagement portion including a proximal portion configured to be disposed on an inside of the fenestrated body, a distal portion configured to be disposed on an outside of the fenestrated body, and an intermediate portion configured to frictionally engage with the opening of fenestrated body;

a flexible tail portion extending from the engagement portion; and a transition portion disposed between the engagement portion and the flexible tail portion, the transition portion having a flexibility greater than the engagement portion and less than the flexible tail portion.

15. The branch stent graft assembly of claim 14, wherein the first portion has a first diameter, the intermediate portion has a second diameter, and the distal portion has a third diameter, the second diameter less than the first diameter and the third diameter in an expanded state.

16. The branch stent graft assembly of claim 15, wherein the first diameter is substantially equal to the third diameter in the expanded state.

\* \* \* \* \*

UNITED STATES PATENT AND TRADEMARK OFFICE
CERTIFICATE OF CORRECTION

| | | |
|---|---|---|
| PATENT NO. | : 11,000,359 B2 | Page 1 of 1 |
| APPLICATION NO. | : 16/265436 | |
| DATED | : May 11, 2021 | |
| INVENTOR(S) | : Casey Torrance | |

It is certified that error appears in the above-identified patent and that said Letters Patent is hereby corrected as shown below:

In the Claims

Column 26, Line 8, Claim 1: before "fenestrated body", insert -- a --

Column 27, Line 6, Claim 14: between "of" and "fenestrated", insert -- the --

Signed and Sealed this
Fifth Day of October, 2021

Drew Hirshfeld
*Performing the Functions and Duties of the
Under Secretary of Commerce for Intellectual Property and
Director of the United States Patent and Trademark Office*